US010654791B2

(12) United States Patent
Garbark et al.

(10) Patent No.: US 10,654,791 B2
(45) Date of Patent: *May 19, 2020

(54) COMPOSITION OF MATTER POLYOLS FOR POLYURETHANE APPLICATIONS

(71) Applicant: PETROLIAM NASIONAL BERHAD, Kuala Lumpur (MY)

(72) Inventors: Daniel B. Garbark, Blacklick, OH (US); Herman Paul Benecke, Columbus, OH (US)

(73) Assignee: PETROLIAM NASIONAL BERHAD, Kuala Lumpur (MY)

( * ) Notice: Subject to any disclaimer, the term of this patent is extended or adjusted under 35 U.S.C. 154(b) by 155 days.

This patent is subject to a terminal disclaimer.

(21) Appl. No.: 14/381,554

(22) PCT Filed: Feb. 28, 2013

(86) PCT No.: PCT/MY2013/000041
§ 371 (c)(1),
(2) Date: Aug. 27, 2014

(87) PCT Pub. No.: WO2013/129910
PCT Pub. Date: Sep. 6, 2013

(65) Prior Publication Data
US 2015/0018444 A1    Jan. 15, 2015

Related U.S. Application Data

(60) Provisional application No. 61/604,298, filed on Feb. 28, 2012.

(51) Int. Cl.
| C07C 57/02 | (2006.01) |
| C07C 67/08 | (2006.01) |
| C08G 18/08 | (2006.01) |
| C08G 18/36 | (2006.01) |
| C08G 18/76 | (2006.01) |
| C08G 18/80 | (2006.01) |
| C09D 175/04 | (2006.01) |
| C09D 175/06 | (2006.01) |
| C11C 1/00 | (2006.01) |
| C11C 1/04 | (2006.01) |
| C11C 3/00 | (2006.01) |
| C11C 3/02 | (2006.01) |
| C08G 101/00 | (2006.01) |

(52) U.S. Cl.
CPC .............. *C07C 67/08* (2013.01); *C07C 57/02* (2013.01); *C08G 18/14* (2013.01); *C08G 18/36* (2013.01); *C08G 18/7657* (2013.01); *C08G 18/8048* (2013.01); *C09D 175/06* (2013.01); *C11C 1/005* (2013.01); *C11C 1/04* (2013.01); *C11C 3/00* (2013.01); *C11C 3/003* (2013.01); *C11C 3/006* (2013.01); *C11C 3/02* (2013.01); *C08G 2101/0008* (2013.01); *C08G 2101/0025* (2013.01)

(58) Field of Classification Search
CPC ........... C07C 67/08; C07C 57/02; C11C 3/02; C08G 18/14; C08G 18/26; C08G 18/7657; C08G 2101/008; C08G 2101/0025; C09D 175/06
See application file for complete search history.

(56) References Cited

U.S. PATENT DOCUMENTS

| 667,043 | A |  | 1/1901 | Steep |
| 2,401,338 | A |  | 6/1946 | Dunmire |
| 2,566,559 | A |  | 9/1951 | Dolnick et al. |
| 2,813,113 | A |  | 11/1957 | Goebel et al. |
| 2,997,493 | A |  | 8/1961 | Huber |
| 3,048,608 | A |  | 8/1962 | Girard et al. |
| 4,061,581 | A |  | 12/1977 | Leleu et al. |
| 4,151,345 | A | * | 4/1979 | Hillegass ............. C08G 18/222 521/124 |
| 4,298,730 | A |  | 11/1981 | Galleymore et al. |
| 4,313,890 | A |  | 2/1982 | Chu et al. |
| 4,865,879 | A | * | 9/1989 | Finlay ...................... B27K 3/15 264/36.15 |
| 5,736,748 | A | * | 4/1998 | Lysenko ............ C08G 18/4866 252/182.24 |
| 5,773,256 | A |  | 6/1998 | Pelenc et al. |
| 5,773,391 | A |  | 6/1998 | Lawate et al. |
| 6,107,500 | A |  | 8/2000 | Prossel et al. |

(Continued)

FOREIGN PATENT DOCUMENTS

| AU | 165032 | 2/1954 |
| CN | 101077856 A | 11/2007 |

(Continued)

OTHER PUBLICATIONS

European Search Report for EP13755591.8 dated Feb. 13, 2015.
International Search Report and Written Opinion for PCT/MY2013/000041 dated Jun. 28, 2013.
Ackman et al., "Ozonolysis of Unsaturated Fatty Acids. I. Ozonolysis of Oleic Acid," Can. J. Chem., 39:1956-1963 (1961).
Yunus et al., "Preparation and Characterization of Trimethylolpropane Esters from Palm Kernel Oil Methyl Esters," J. Oil Palm Research, 15(2):42-49 (2003).
Spyros, A., "Quantitative Determination of the Distribution of Free Hydroxylic and Carboxylic Groups in Unsaturated Polyester and Alkyd Resins by 31 P-NMR Spectroscopy," J. Appl. Polym. Sci., 83:1635-1642 (2002).

(Continued)

Primary Examiner — Melissa A Rioja
(74) Attorney, Agent, or Firm — Pepper Hamilton LLP

(57) ABSTRACT

There are provided ester polyols prepared from the esterification of ozone acids and branched primary polyols. There are also provided ester polyol esters prepared from an ester polyol of the invention and further esterifying the ester polyol with at least one carboxylic acid to produce at least one ester polyol ester. There are also provided rigid or flexible foams prepared using the ester polyols and/or ester polyol esters of the invention. There is also provided a coating prepared from the ester polyols and/or ester polyols esters of the invention.

24 Claims, 6 Drawing Sheets

(56) References Cited

U.S. PATENT DOCUMENTS

| | | | |
|---|---|---|---|
| 6,362,368 | B1 | 3/2002 | Frische et al. |
| 7,125,950 | B2 | 10/2006 | Dwan'Isa et al. |
| 7,192,457 | B2 | 3/2007 | Murphy et al. |
| 7,241,914 | B2 | 7/2007 | Wartini et al. |
| 7,589,222 | B2 | 9/2009 | Narayan et al. |
| 2004/0167343 | A1 | 8/2004 | Halpern et al. |
| 2005/0112267 | A1 | 5/2005 | Kian et al. |
| 2006/0194974 | A1 | 8/2006 | Narayan et al. |
| 2009/0216040 | A1 | 8/2009 | Benecke et al. |
| 2009/0239964 | A1* | 9/2009 | Sasaki ............... C08G 18/4804 521/117 |
| 2010/0087350 | A1 | 4/2010 | Sonnenschein et al. |
| 2010/0117022 | A1 | 5/2010 | Carr et al. |
| 2011/0077350 | A1* | 3/2011 | Malotky ................ C08J 3/05 524/588 |
| 2011/0269979 | A1 | 11/2011 | Benecke et al. |
| 2011/0269981 | A1 | 11/2011 | Benecke et al. |
| 2011/0269982 | A1 | 11/2011 | Benecke et al. |
| 2012/0184758 | A1 | 7/2012 | Krull et al. |
| 2015/0005520 | A1 | 1/2015 | Benecke et al. |
| 2015/0018260 | A1 | 1/2015 | Benecke et al. |
| 2015/0080599 | A1 | 3/2015 | Garbark et al. |
| 2015/0087850 | A1 | 3/2015 | Benecke et al. |

FOREIGN PATENT DOCUMENTS

| | | |
|---|---|---|
| CN | 101195577 A | 6/2008 |
| CN | 201343513 Y | 11/2009 |
| CN | 101812349 A | 8/2010 |
| CN | 101899160 A | 12/2010 |
| CN | 102010772 A | 4/2011 |
| EP | 0010333 A1 | 4/1980 |
| EP | 1260497 A2 | 11/2002 |
| EP | 1529828 A1 | 5/2005 |
| EP | 1533360 A1 | 5/2005 |
| GB | 915461 | 1/1963 |
| JP | S57185235 A | 11/1982 |
| JP | 04018049 A | 1/1992 |
| JP | 2008013546 A | 1/2008 |
| KR | 10-2008-0023290 A | 3/2008 |
| MY | 140833 A | 1/2010 |
| WO | 1993024585 A1 | 12/1993 |
| WO | 98/50338 A1 | 11/1998 |
| WO | 2000039068 A1 | 7/2000 |
| WO | 2004087847 A1 | 10/2004 |
| WO | 2006-093874 A2 | 9/2006 |
| WO | 2006093874 A2 | 9/2006 |
| WO | 2007-027223 A2 | 3/2007 |
| WO | 2007027223 A2 | 3/2007 |
| WO | 2010-078505 A1 | 7/2010 |
| WO | 2010/085545 A1 | 7/2010 |
| WO | 2010078491 A1 | 7/2010 |
| WO | 2010078493 A1 | 7/2010 |
| WO | 2010078498 A1 | 7/2010 |
| WO | 2010078505 A1 | 7/2010 |
| WO | 2013129907 A1 | 9/2013 |
| WO | 2013129908 A1 | 9/2013 |
| WO | 2013129909 A1 | 9/2013 |
| WO | 2013129910 A1 | 9/2013 |
| WO | 2013129911 A1 | 9/2013 |
| WO | 2014133380 A8 | 9/2014 |

OTHER PUBLICATIONS

PCT International Search Report and Written Opinion for International Patent Application No. PCT/MY2013/000038 (dated Jun. 27, 2013).
PCT International Search Report and Written Opinion for International Patent Application No. PCT/MY2013/000039 (dated Jun. 27, 2013).
PCT International Search Report and Written Opinion for International Patent Application No. PCT/MY2013/000040 (dated Jun. 28, 2013).
PCT International Search Report and Written Opinion for International Patent Application No. PCT/MY2013/000041 (dated Jun. 28, 2013).
PCT International Search Report and Written Opinion for International Patent Application No. PCT/MY2013/000042 (dated Jun. 28, 2013).
International Preliminary Report on Patentability for International Patent Application No. PCT/MY2013/000038 (dated Sep. 12, 2014).
International Preliminary Report on Patentability for International Patent Application No. PCT/MY2013/000039 (dated Sep. 12, 2014).
International Preliminary Report on Patentability for International Patent Application No. PCT/MY2013/000040 (dated Sep. 12, 2014).
International Preliminary Report on Patentability for International Patent Application No. PCT/MY2013/000041 (dated Sep. 12, 2014).
International Preliminary Report on Patentability for International Patent Application No. PCT/MY2013/000042 (dated Sep. 12, 2014).
Office Action for U.S. Appl. No. 14/381,530 dated Dec. 10, 2015.
Gmehling et al., "Azeotropic Data for Binary Mixtures", Handbook of Chemistry and Physics (96th Edition, 2015-2016), pp. 6-210 to 6-228.
Third Party Submission for U.S. Appl. No. 14/381,554 dated Jul. 13, 2015.
Extended European Search Report for EP13755362.4 dated Aug. 21, 2015.
Extended European Search Report for EP13754711.3 dated Sep. 3, 2015.
PCT International Search Report and Written Opinion corresponding to PCT/MY2014/000026, filed Feb. 28, 2014 (dated May 21, 2014).
Akerman et al., "Biolubricant Synthesis Using Immobilised Lipase: Process Optimisation of Trimethylolpropane Oleate Production," Process Biochem. 46:2225-2231 (2011).
Translated Office Action for Chinese Application No. 201380022561.5, dated Sep. 6, 2015.
Search Report and Written Opinion for Singapore Application No. 11201405261T, dated Sep. 10, 2015.
Search Report and Written Opinion for Singapore Application No. 11201405268P, dated Oct. 1, 2015.
Office Action for U.S. Appl. No. 14/381,545 dated Jun. 2, 2017.
Office Action for EP 13755591.8 dated Apr. 20, 2017.
Third Party Observations for EP 13755591.8 dated Dec. 1, 2015.
Office Action for U.S. Appl. No. 14/381,539 dated May 29, 2015.
Translated Office Action for JP 2014-559854 dated Jul. 11, 2016.
Written Opinion and Search Report for SG 11201405266W dated Sep. 9, 2015.
Written Opinion for SG 11201405266W dated May 26, 2016.
Translated Office Action for CN 201380022554.5 dated Sep. 8, 2015.
Translated Office Action for CN 201380022554.5 dated May 30, 2016.
Translated Office Action for CN 201380022554.5 dated Sep. 5, 2016.
Office Action for U.S. Appl. No. 14/381,564 dated Jun. 3, 2015.
Office Action for U.S. Appl. No. 14/771,137 dated Jan. 11, 2016.
Office Action for U.S. Appl. No. 14/771,137 dated Oct. 12, 2016.
Office Action for China Application No. 201380022561.5 (dated Apr. 18, 2016).
Sebedio et al., "Comparison of the Reaction Products of Oleic Acid Ozonized in BCl3—, HCl— and BF3—MeOH Media," Chemistry and Physics of Lipids 35(1):21-28 (1984) (Abstract only).
English translation of First Office Action for China Application No. 201611187592.8 (dated Jun. 5, 2019).
Xijiao Wang, "Standard Application Manual for Coatings and Pigments (vol. I)", First Edition, Yi Wen Publishing Military, p. 439 (2005) (see partial English translation on pp. 4-5 of attached NPL Ref. 1, addressing claim 1).

* cited by examiner

Figure 1. Oxidative Cleavage of Typical Fatty Acid Components to Form Oxidation Acids Followed by Esterification with Glycerin under Relatively High Hydroxyl/Carboxyl Ratios Figure 2. Ester Polyols Formed from Esterification of Fatty Acid-Derived Oxidation Acids with Glycerin under Relatively Low Glycerin to Ozone Acid Ratios Showing Capping with Monofunctional Acids and Branching Involving Glycerin

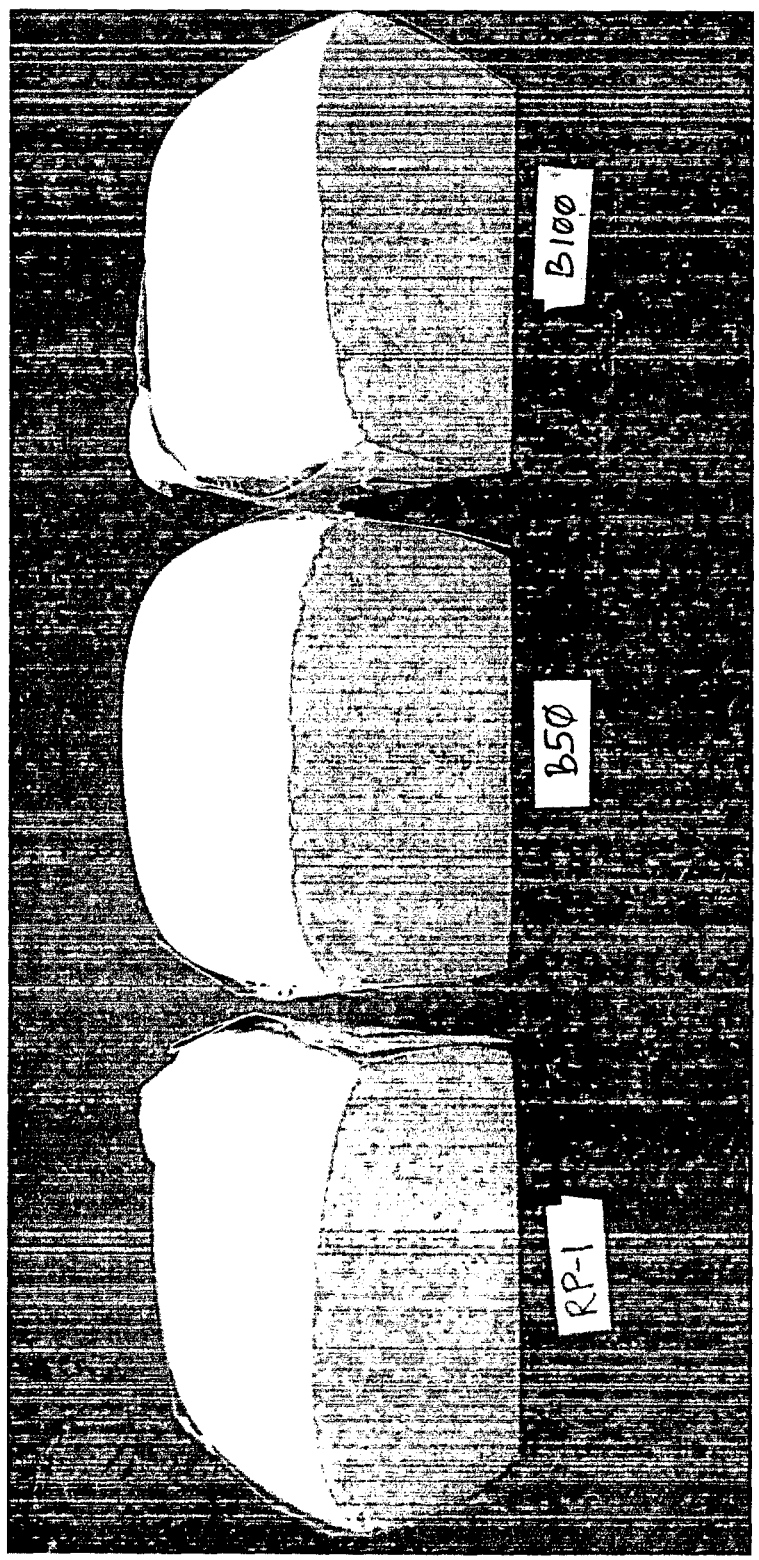
Figure 4. Photograph of rigid foam samples prepared for formulation screening

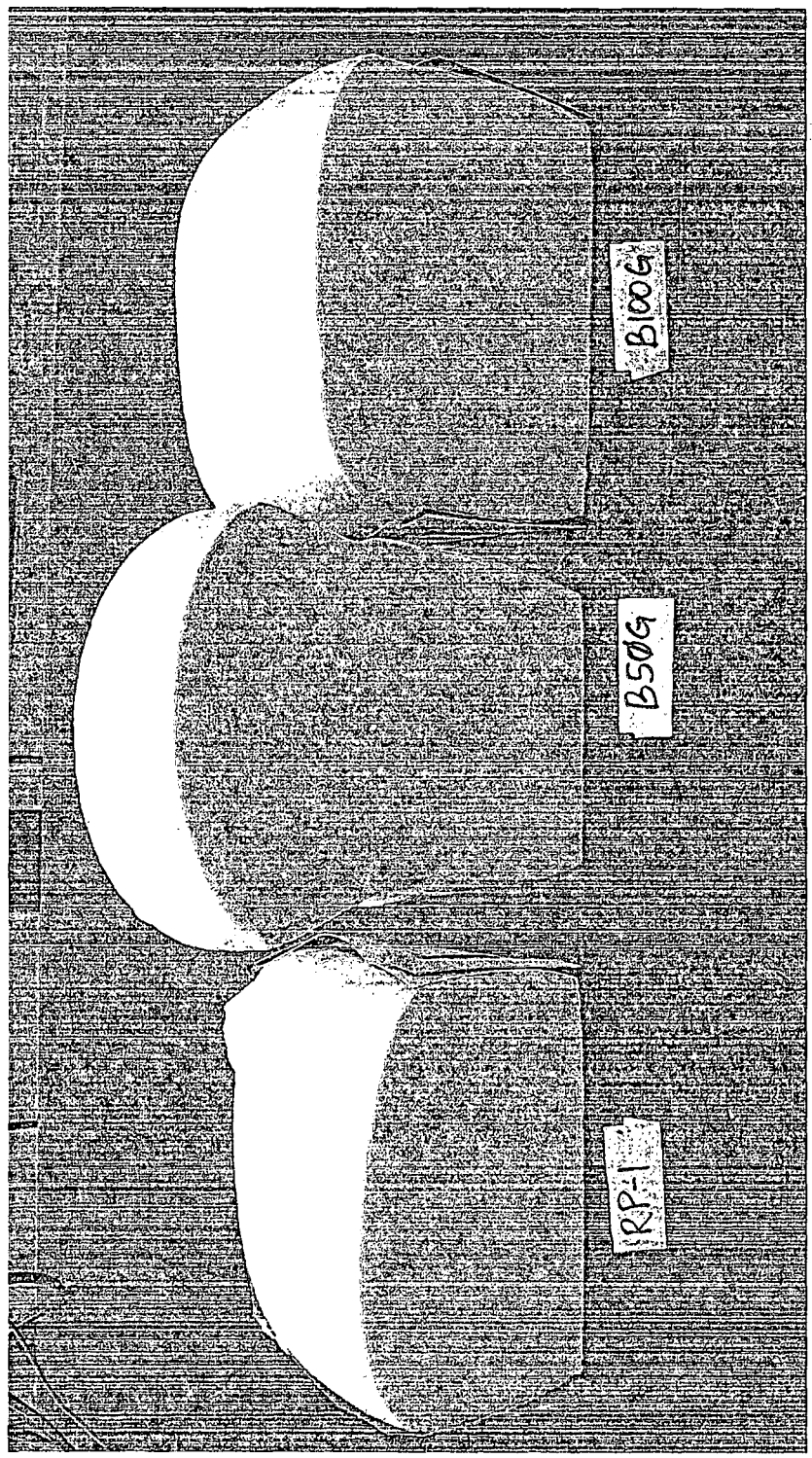
Figure 5. Photograph of rigid foam samples prepared for formulation screening with glycerol

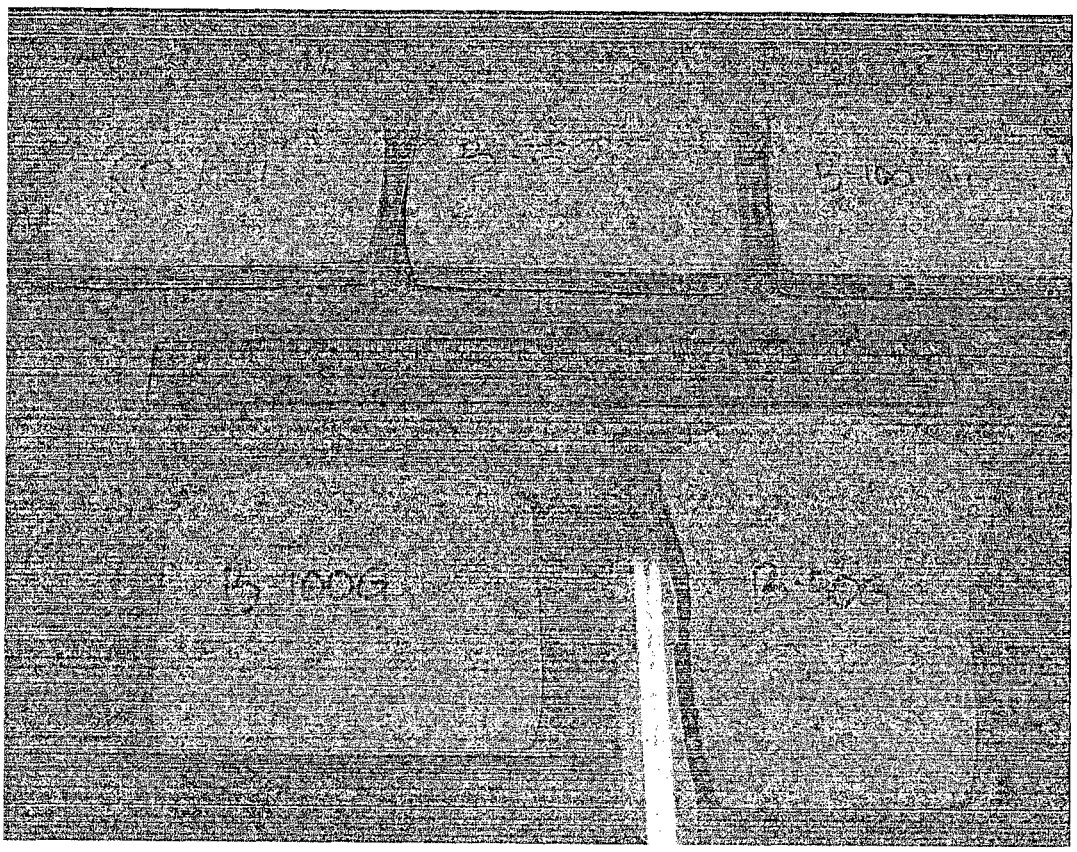
Figure 6. Photograph of rigid foam samples prepared for formulation screening after heating at 120°C for 60 minutes

COMPOSITION OF MATTER POLYOLS FOR POLYURETHANE APPLICATIONS

This application is a national stage application under 35 U.S.C. 371 from PCT/MY2013/000041, filed Feb. 28, 2013, which claims the benefit of U.S. Provisional Patent Application Ser. No. 61/604,298, filed Feb. 28, 2012, each of which is hereby incorporated by reference in its entirety.

FIELD OF THE INVENTION

The present invention relates to methods for the preparation of ester polyols, in particular ester polyols formed from the ozonolysis of fatty acids derived from vegetable oils or fats that are subsequently esterified with primary polyols. The ester polyols are useful in a variety of applications, particularly in the production of polyurethane foams and/or coatings.

BACKGROUND OF THE INVENTION

The listing or discussion of an apparently prior-published document in this specification should not necessarily be taken as an acknowledgement that the document is part of the state of the art or is common general knowledge.

The present invention provides a process using renewable resources, such as, oils and/or fats, fatty acids, and fatty acid esters derived from plants and animals to produce ester polyols in essentially quantitative yields via the ozonolysis process. The ester polyols are very useful for the production of polyurethane-based coatings and foams, as well as, polyester applications.

Most of the current polyurethanes foams are produced from petroleum based polyol. It is desirable to replace a portion or all of the petroleum polyol with a polyol derived from a plant or animal source when producing polyurethane foams or coatings. Polyols derived from plant or animal sources are known as biopolyols. Palm oil, which is primarily composed of saturated and unsaturated fatty acids chains, is a potential precursor for the production of polyols by using these double bonds to introduce hydroxyl groups by a number of chemical processes. It is desirable that this hydroxyl functionality be primary rather than secondary to enhance polyol reactivity in the preparation of polyurethanes by reacting with isocyanates. Other examples of vegetable and animal fats include soybean oil, safflower oil, linseed oil, corn oil, sunflower oil, olive oil, canola oil, sesame oil, cottonseed oil, mustard oil, camelina oil, jatropha oil, peanut oil, coconut oil, rapeseed oil, Chinese tallow oil, tung oil, castor oil, algae oil, wheat germ oil, soya oil, hemp oil, fish oil, lard, tallow, or the like and a mixture thereof.

Byproducts of the above-mentioned oils and lipids, such as, palm fatty acid distillates (PFAD), palm kernel fatty acid distillates, fractionated palm fatty acid distillate, and fractionated palm kernel fatty acid distillate, fatty acids of soybean oil, palm fatty acid alkyl esters, alkyl esters of any biobased lipids, or the like, or a mixture, or a fraction thereof may be used as a source of fatty acids.

The use of natural oils to produce ester polyols has been disclosed in several patents. In the production of polyols, natural oils offer two reactive sites, the double bond of unsaturated fatty acids, and the carboxyl ester group linking the fatty acid to the glycerine. U.S. Pat. No. 7,125,950 describes a solvent free process for making a fatty acid polyester polyol composition useful for the preparation of polyurethanes via the transesterification process. In this patent, natural oil is reacted with a multifunctional hydroxyl compound in the presence of an alkali metal or alkaline earth metal base or salt catalyst in absence of a solvent. The hydroxyl content of the prepared composition depends on the amount of the multi-functional hydroxyl compound used in the preparation.

PCT Pub. No. WO2007027223 describes various solvent-based approaches to prepare product ester polyols from plant or animal sources. PCT Pub. No. WO2007027223 disclose the production of 1-monoglycerides, 2-monoglycerides and diglycerides from the ozonolysis of soybean oil in the presence of a variety of primary polyols such as glycerin and either Bronsted or Lewis acids as catalysts. The polyols are reacted with polyisocyanates, polyacids, or polyesters to produce polyurethane and polyester coatings. However, WO2007027223 does not disclose or suggest the use of branched primary polyols.

US Patent Application No. US 2006/0194974 described a method for making a modified triglyceride which comprises reacting vegetable oil with ozone in a reaction mixture in the presence of a hydroxylated compound and alkaline catalyst. The ozone and the vegetable oil react to cleave double bonds of fatty acid groups within the triglyceride and the hydroxylated compound, in the presence of the catalyst, is added to terminal carbons of the cleaved double bonds through an ester covalent bond.

There still is a need in this technical field for ester polyols with improved performance characteristics for rigid and flexible foams and polyurethane coatings. Ester polyols prepared from feedstock containing high amounts of saturated fatty acids tend to undergo significant phase separation, resulting in the precipitation of waxy solids. Such ester polyols may then require additional process steps to make them suitable for processing into more useful products like coatings and foams. It is thus desirable to further investigate methods for improving the preparation of preparing ester polyols, in particular ester polyol which may comprise high amounts of saturated fatty acids.

SUMMARY OF THE INVENTION

The present invention addresses the problem in the art and provides a method for the preparation of ester polyols comprising esterifying at least one ozone acid with at least one primary polyol to produce an ester polyol.

In particular, the present inventors have found that by incorporating branched primary polyols into the structure of the ester polyols it is possible to obtain ester polyols with increased resistance to phase separation and precipitation.

In one aspect the invention provides a method of preparing at least one ester polyol, comprising esterifying at least one ozone acid with at least one branched primary polyol to produce an ester polyol.

In a further aspect, the invention provides a method of preparing an ester polyol ester, the method comprising preparing an ester polyol by esterifying at least one ozone acid with at least one branched primary polyol, and further esterifying the resulting ester polyol with at least one carboxylic acid to produce at least one ester polyol ester.

In a yet further aspect, the invention provides a method of preparing a foam, the method comprising preparing an ester polyol ester by esterifying at least one ozone acid with at least one branched primary polyol, further esterifying the resulting ester polyol with at least one carboxylic acid, and further reacting the resulting ester polyol ester with at least one compound selected from an petroleum polyol, a cross-linking agent, a cell opening additive and an isocyanate, or a mixture thereof.

According to one aspect, the present invention provides an ester polyol obtained or obtainable by the above methods.

According to one aspect, the present invention provides an ester polyol, wherein the ester polyol comprises the reaction product of at least one ozone acid; and at least one branched primary polyol.

This invention also provides a method for making polyurethane foams from the ester polyols compositions. Ester polyols having a unique branched architecture and the use and properties provided by the use of branched primary polyols are described herein. The foams and/or polyurethane coating are prepared using at least one ester polyol component, which may used without other ester polyols or may be a blend of bio-based ester polyol and petroleum polyol.

According to one aspect, the invention provides a foam obtained or obtainable according to the above methods.

According to one aspect, the invention provides a foam, wherein the foam is prepared from an ester polyol according to any of the above methods and/or an ester polyol ester according to any of the above methods.

According to one aspect, the invention provides a foam, wherein the foam comprises the reaction product of at least one ozone acid and at least one branched primary polyol.

According to one aspect, the present invention provides an ester polyol, wherein the ester polyol has the formula of:

There is also provided at least one foam comprising an ester polyol according to any aspect of the invention. In particular, the foam according to the invention may further comprise at least one petroleum polyol.

According to another aspect, there is provided a polyurethane coating, prepared using an ester polyol according to the invention.

According to another aspect, there is provided a method of reducing the separation of a composition comprising at least one ester polyol in a single phase into two or more phases. The method comprises esterifying at least one ozone acid with at least one branched primary polyol to produce the at least one ester polyol, thereby reducing the phase separation of the at least one ester polyol.

According to a particular embodiment, the method of reducing phase separation of the ester polyol composition involves a single liquid phase.

According to another particular embodiment, the method of reducing phase separation of the ester polyol composition results in the ester polyol composition not substantially separating into more than one phase.

According to another particular embodiment, the method of reducing phase separation of the ester polyol composition involves letting the composition achieve a temperature of from about 20° C. to about 80° C.

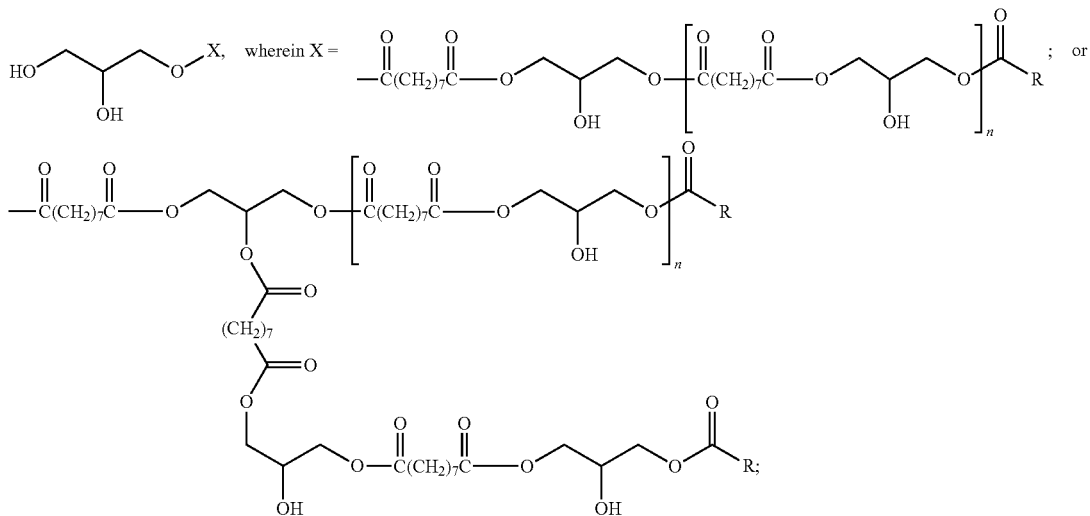

and

R is selected from palmitate, stearate, hexanoate, pelargonate, and propionate monoesters and azelate diesters, wherein n is from 1 to about 3 esters.

In particular, the ester polyol according to the invention may comprise the reaction product of: at least one ozone acid; and at least one primary polyol.

In particular, the primary polyol is a branched primary polyol. More in particular, a branched primary polyol according to the invention is at least one branched primary polyol selected from the group consisting og 2-methyl-1,3-propanediol (2-MePG); trimethylolpropane (TMP); di-trimethylolpropane (Di-TMP); pentaerythritol (PE); dipentaerythritol diPE) and neopentyl glycol (NPG); or a mixture thereof.

The ester polyol according to the invention may have a hydroxyl value (HV) of from about 20 to about 450 mg KOH/g.

In another aspect of the invention, the ester polyols created by the method of the present invention may be reacted with isocyanates to form polyurethanes. The ester polyols produced by the present invention have a range of hydroxyl content from 20-450 mg KOH/g which will lead to polyurethane materials having a range of physical and mechanical properties, suitable for a variety of applications.

In another aspect of the invention, a method of preparing at least one ester polyol comprises esterifying at least one ozone acid with at least one primary polyol to produce an ester polyol.

In a further aspect of the invention, a method of preparing an ester polyol ester comprises preparing an ester polyol by esterifying at least one ozone acid with at least one primary polyol, and further esterifying the ester polyol with at least one carboxylic acid to produce at least one ester polyol ester.

In yet another aspect of the invention, a method of preparing a foam comprises first preparing an ester polyol by esterifying at least one ozone acid with at least one primary polyol, further esterifying the ester polyol with at least one carboxylic acid to produce at least one ester polyol ester, and further reacting the ester polyol ester with at least one compound selected from an petroleum polyol, a cross-linking agent, a cell opening additive and an isocyanate, or a mixture thereof.

In an embodiment of the invention, the method of preparing the ester polyol comprises esterifying the ozone acid(s) with at least two primary polyols.

BRIEF DESCRIPTION OF THE FIGURES

The accompanying figures, which are incorporated in and constitute a part of this specification, illustrate aspects of the invention and, together with a general description of the invention given above, and the detailed description given below, serve to explain the invention.

FIG. 4 is a photograph of rigid foam samples prepared for formulation screening.

FIG. 5 is a photograph of rigid foam samples prepared for formulation screening with glycerol.

FIG. 6 is a photograph of rigid foam samples prepared for formulation screening after heating at 120° C. for 60 minutes.

DEFINITIONS

Figure 1:
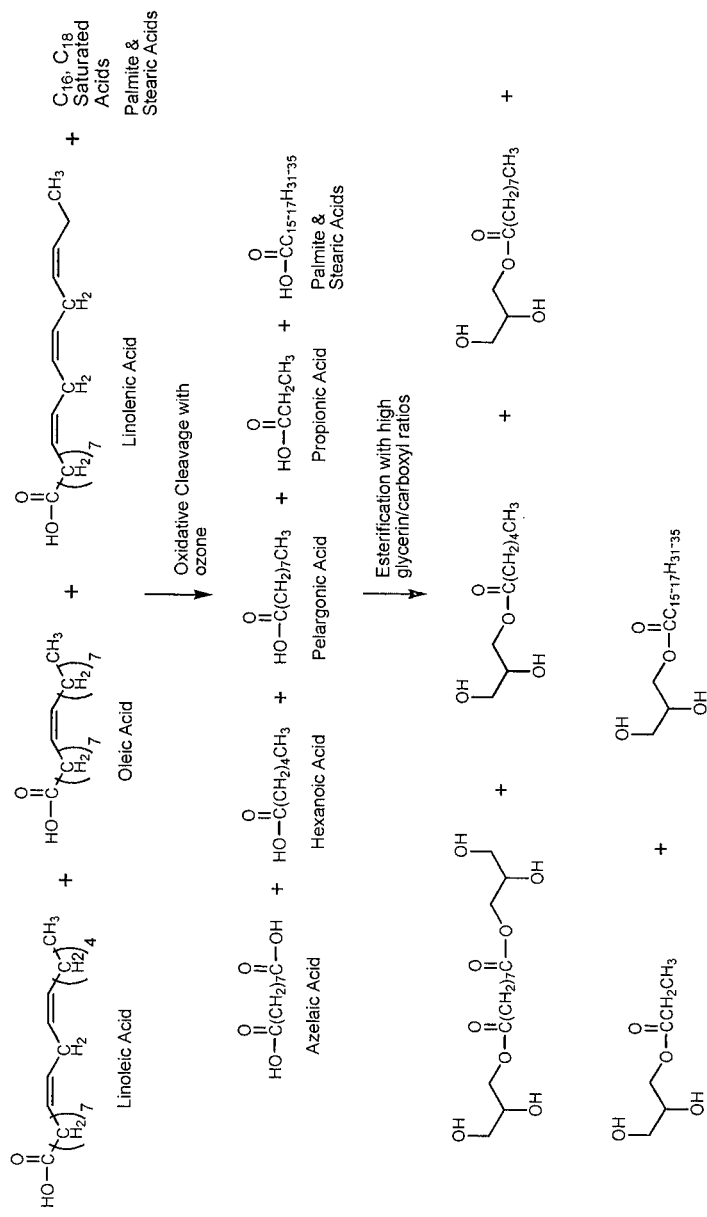
FIG. 1 is a schematic of the ester polyols formed from the esterification of ozone acids with glycerin under relatively high hydroxyl/carboxyl ratios.

When used in all aspects and embodiments herein, the term "comprises" or variants thereof can be replaced by the term "consists of" or variants thereof and vice versa.

For the purposes of this invention, "Hydroxyl Value" (HV) is a measure of the number of hydroxyl groups per unit weight of an ester polyol. It is obtained by acetylating all polyol hydroxyl groups and subsequently titrating the acetylated hydroxyl groups with potassium hydroxide. It is expressed in units of mg potassium hydroxide per gram of sample. Conversion of this weight of potassium hydroxide to the corresponding number of moles potassium hydroxide provides the number of moles of hydroxyl groups per gram of sample.

For the purposes of this invention, "Acid Value" (AV) is a measure of the number of acid groups present per unit weight in a sample. It is obtained by a direct titration with standardized potassium hydroxide solution to a phenolphthalein end point and is expressed in mg potassium hydroxide per gram of sample where the moles of potassium hydroxide are equal to moles of titratable acid groups.

For the purposes of this invention, "phase separation" refers to the process by which some components in a composition in a single phase separate into two or more phases. The resulting two or more phases may have different concentrations of compounds. For example, a liquid composition of ester polyols may undergo precipitation of some ester polyols as solids, reducing the amount of ester polyols that remain in a liquid state. This would result in a liquid phase and a solid phase, both of which may comprise ester polyols. Such ester polyols may then require additional process steps to make them suitable for processing into more useful products like coatings and foams, for example heating them to cause the solid ester polyols to return to a liquid state.

For the purposes of this invention, Petroleum Polyols are polyols derived from petroleum resources. Polyether polyols and polyester polyols are two major kinds of petroleum polyols consumed in the global polyols market. In an example of a polyether polyol, an initiator like ethylene glycol, propylene glycol or glycerin reacts with an alkylene oxide to produce a polyether polyol with a primary hydroxyl group. Examples of polyether polyols include Polytetramethylene etherglycol (PTMEG), Polypropylene oxide glycol (PPO) and polybutylene oxide glycol (PBO). In an example of a polyester polyol, a glycol such as 1,6 hexanediol or a polyols such as glycerin reacts with diester or diacid to form a primary polyester polyol.

For the purposes of this invention, Isocyanates are organic compounds containing the functional group —N=C=O. For example, Methylene diphenyl diisocyanate (MDI) and toluene diisocyanate (TDI) are two major kinds of isocyanates consumed in the global isocyanate market. Commercially available isocyanates such as Mondur MRS-2, Rubinate 1680 and Rubinate M may be used. Other types of isocyanates, like 1,6-hexane diisocyanate (HDI), isophorone diisocyanate (IPDI), 1,5-napthalene diisocyanate (NDI), 1,4-phenylene diisocyanate (PDI) are also used in different applications.

For the purposes of this invention, cell opening additives are chemical agents used in polyurethane manufacturing to improve dimensional stability of the polyurethane. Examples are commercially available cell opening additives such as Lumulse POE 26, Niax I-670 but also any suitable cell opening additives known to a person skilled in the art, such as organic acids, such as benzoic, salicylic, or adipic, alkali metal salts of these acids, and siloxane-oxyalkylene copolymers.

DETAILED DESCRIPTION OF THE INVENTION

The present invention relates to methods for the preparation of ester polyols. In particular, the invention related to ester polyols formed from the ozonolysis of fatty acids that are subsequently esterified with primary polyols. The fatty acids used in the present invention may be derived from renewable resources especially from palm-based materials such as palm oil and Palm Fatty Acid Distillates (PFAD). However, the present invention is not limited to the use of palm oil and/or PFAD. The ester polyols according to the invention are useful in a variety of applications, particularly in the production of polyurethane foams and/or coatings. Rigid to flexible foams can be produced depending on the hydroxyl value of the ester polyol intermediates. The ester polyols are produced from the esterification of ozone acids. In particular, feedstock, such as, fractionated palm fatty acid distillate (PFAD) or High Oleic Fatty acid mixture undergo an ozonolysis reaction to produce their respective ozone acids.

According to a particular aspect, the present invention seeks to incorporate branched primary polyols into the structure of the ester polyols so as to obtain ester polyols with increased resistance to phase separation and precipitation. As a consequence, ester polyols undergo a reduced or no phase separation and may be processed directly into polyurethanes and/or other useful materials.

Accordingly, there is provided a method of preparing at least one ester polyol, comprising esterifying at least one ozone acid with at least one branched primary polyol to produce an ester polyol.

In a further aspect, the invention provides a method of preparing an ester polyol ester, the method comprising preparing an ester polyol by esterifying at least one ozone acid with at least one branched primary polyol, and further esterifying the resulting ester polyol with at least one carboxylic acid to produce at least one ester polyol ester.

In a yet further aspect, the invention provides a method of preparing a foam, the method comprising preparing an ester polyol ester by esterifying at least one ozone acid with at least one branched primary polyol, further esterifying the resulting ester polyol with at least one carboxylic acid, and further reacting the resulting ester polyol ester with at least one compound selected from an petroleum polyol, a crosslinking agent, a cell opening additive and an isocyanate, or a mixture thereof.

The method of the present invention utilizes ozone acids expected to be produced from oxidative ozonolysis process, for example as described by U.S. Pat. No. 2,813,113 and related patents. In particular, the fatty acids derived from vegetable oil and/or animal oils are initially subjected to oxidative cleavage so that all double bonds are cleaved and converted to carboxylic acid groups. In the oxidative cleavage of unsaturated fatty acids derived vegetable oil or animal oils, a mixture of diacids and monoacids (referred to ozone acids) are produced. Palm fatty acid distillates (PFAD) may be used as a starting material or feedstock and source of fatty acids. Triglycerides, such as, palm oil are another source of fatty acids. PFAD which is composed primarily of fatty acids but also contains mono-, di-, and triglycerides can be hydrolyzed to produce fatty acids. Examples of triglycerides include vegetable oil and animal fat. In particular, the triglyceride may be selected from soybean oil, safflower oil, linseed oil, corn oil, sunflower oil, olive oil, canola oil, sesame oil, cottonseed oil, mustard oil, camelina oil, jatropha oil, peanut oil, coconut oil, rapeseed oil, Chinese tallow oil, tung oil, castor oil, algae oil, wheat germ oil, soya oil, hemp oil, fish oil, lard tallow, duck fat, butter, or the like and a mixture thereof. Other source of fatty acids include fractionated palm fatty acid distillate, fatty acids of soybean oil, palm fatty acid alkyl esters, alkyl esters of any biobased lipids, or the like, or a mixture, or a fraction thereof.

It is known that the oxidative ozonolysis of fatty acids as specified in U.S. Pat. No. 2,813,113 results in generation of carboxylic acid functionality at each of the two carbon atoms that originally comprise the double bonds in each fatty acid. Examples of individual ozone acids that will be produced from the ozonolysis of each type fatty acids can thus be predicted. This knowledge allows one to calculate and predict the specific percentages of the diacid azelaic acid and all monoacids resulting from oxidative ozonolysis of any fatty acid feedstock composition. Thus, different ozone acid compositions can be simulated by mixing the calculated amounts of diacid (azelaic acid) and monoacids expected from the oxidative ozonolysis of any feedstock. We refer to these mixtures as simulated ozone acids. In an aspect of the present invention, mixtures of simulated difunctional and monofunctional ozone acids were used to prepare the ester polyols for evaluation in polyurethane applications. One specific simulated ozone acid mixture used to prepare ester polyols was the mixture predicted to be obtained from the oxidative ozonolysis of palm-based fatty acid.

Some desirable feedstocks have high concentration of saturated fatty acids that lead to formation of solid ester polyols. This was found to be mitigated by admixture of sterically hindered primary polyols or branched primary polyols such as 1,2-propanediol or 2-methyl-1,3 propanediol. In general ester polyols prepared from full composition fatty acid mixtures required significantly more branched alternate primary polyols such as 2-methyl-1,3-propanediol (abbreviated Me-PG) than fractionated composition fatty acid mixtures to reduce or prevent phase separation.

In the present invention, the ester polyols have a unique structure because they can incorporate branched primary polyols. The branched primary polyols are effective in inhibiting and/or reducing phase separation in chains of hydrocarbon, particularly. primary polyols are important when preparing polyols from palm feedstock because palm feedstock contains high amounts of saturated fatty acids that cause phase separation. In particular, a branched primary polyol according to the invention is at least one branched primary polyol selected from the group consisting og 2-methyl-1,3-propanediol (2-MePG); trimethylolpropane (TMP); di-trimethylolpropane (Di-TMP); pentaerythritol (PE); dipentaerythritol diPE) and neopentyl glycol (NPG); or a mixture thereof. More in particular, a branched primary polyols according to the invention comprises at least one of 2-methyl-1,3 propanediol, Trimethylolpropane (TMP) and neopentyl glycol, or a mixture thereof.

Polyols incorporating branched primary polyols into the structure of the ester polyols according to the invention achieved high bio based content in the polyurethane foams and/or coatings while maintaining required performance characteristics despite the potentially problematic amounts of high levels of saturated fatty acids (e.g. palmitic acid). In the present invention, the polyol esters can also have branched structures that hinder close packing of the polyester chains, thus inhibiting crystallization. Further, the present invention demonstrates that the amount of carboxylic acid and primary polyol used in esterification affects the viscosities, molecular weights, and crosslinking of the ester polyol. Foams and polyurethane coatings formed from ester polyols of the present invention have good physical properties, such as, density, thermal conductivity, tensile strength, and elongation at break.

The approach and methodology as proposed in the present invention is to produce a unique class of intermediates composed of ester polyols derived from the esterification of primary polyols with various carboxylic acids. Due to the unique structure of the ester polyols, the viscosities, hydroxyl values, and molecular weight of the intermediates can be adjusted. This factor allows the development of polyols having a wide range of hydroxyl values (HVs). By adjusting the properties of the ester polyols, the functionality of the foams and/or polyurethane coatings can be adjusted to fit use specifications.

Further, the present invention shows that the amount of carboxylic acid and the primary polyols used in esterification affects the viscosities, molecular weights, and crosslinking of the ester polyol. The present invention will also show that modifying the parameter of hydroxyl to carboxyl groups in the esterification of excess primary polyols with ozone acids to form ester polyols results in modification of the hydroxyl value (HV), viscosity and structure of the ester polyol. Another aspect of the present invention is forming an ester polyol with either a linear or branched structure. These factors allow the development of foams derived from the polyols having a wide range of properties.

Figure 3:
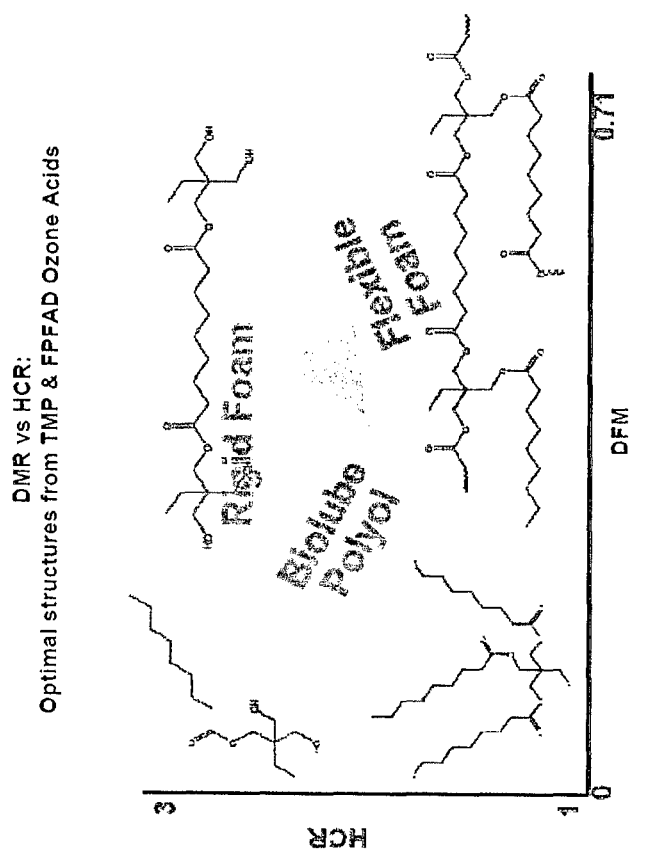
FIG. 3 illustrates the idealized structures formed from TMP and Fractionated PFAD Ozone acids with respect to Difunctional/Monofunctional Ratio (DMR) and hydroxyl/carboxyl ratio (HCR) concentrations.

The versatility of the polyol process is a key feature in being able to develop biopolyols which span a range of properties and characteristics and allowing use in different applications. For example, rigid foam polyols typically have hydroxyl values (HV) in the 250-450 KOH/g range. Flexible foam polyols typically have hydroxyl values (HV) in the 20-150 KOH/g range, in particular 50-150 KOH/g range, and coating polyols typically have hydroxyl values (HV) in the 150-250 range. These characteristics are attainable by selecting the input compounds and adjusting their Difunctional Monofunctional ratio (DMR) and hydroxyl/carboxyl ratio (HCR) as illustrated in FIG. 3.

In all polyols, the presence of hydroxyl functionality and the selection of HCR are responsible for excess hydroxyl content or hydroxyl value (HV) of the product polyol. This is achieved by the relative amounts of primary polyol and the amounts of carboxylic acid group containing compounds, both diacids and monoacids, in the polyol synthesis. Thus, the higher the amount of primary polyol, the higher the resulting hydroxyl value (HV) of the product polyol. In the following examples, the simulated ozone acids expected from the oxidative ozonolysis of fractionated Palm Fatty Acid Distillate (PFAD) and a mixture of fractionated high oleic fatty acid were esterified with the branched primary polyols 2-methyl-1,3 propanediol and trimethylolpropane (TMP) to generate ester polyols.

FIG. 1 shows the oxidative cleavage of a fatty acid source, such as, vegetable oil or animal fat, containing linoleic, oleic, linolenic, and saturated fatty acids. The products of the oxidative ozonolysis are the ozone acids azelaic acid (1,9-nonadioic acid), hexanoic acid, pelargonic acid (nonanoic acid), propanoic acid, and the original saturated fatty acids palmitic and stearic acids. Palmitic and stearic acids do not change during oxidative ozonolysis. Cleavage occurs at the double bond sites of the fatty acids so that some of the same ozone acids are produced from different fatty acids. For example, linoleic acid produces azelaic and hexanoic acids while oleic acid produces azelaic and pelargonic acids. Malonic acid (a $C_3$ diacid) is formed from both linoleic and linolenic acids and decomposes to acetic acid (not shown) and carbon dioxide at the temperatures used in the second stage of oxidative ozonolysis. However acetic acid is not shown in FIG. 1 or 2 since the purification process used in the commercial production of ozone acids can be readily adjusted to remove acetic acid.

When this mixture of ozone acids is esterified with glycerin under relatively high glycerin concentrations relative to the ozone acid concentrations, the major glyceride products are the type of monoglycerides shown. These monoglycerides are known as ester polyols. Inherently, monoglycerides will have higher hydroxyl values (HV) than the diglycerides and triglycerides shown in FIG. 2. The high HV ester polyol structures are used in applications including polyurethane rigid foams. The monoglyceride-based ester polyols represent a limiting type of structure of polyols as compared to FIG. 2. However, small amounts of polyol ester structures shown in FIG. 2 can be formed under conditions of high glycerin to ozone acid concentrations. Their relative concentrations of the ester polyols found in FIGS. 1 and 2 will specifically depend on the glycerin to ozone acid concentration. For FIGS. 1 and 2, molecular modeling is used to predict the relative concentrations of ester polyol structures formed at different ratios of glycerin to ozone acid concentrations.

Figure 2:
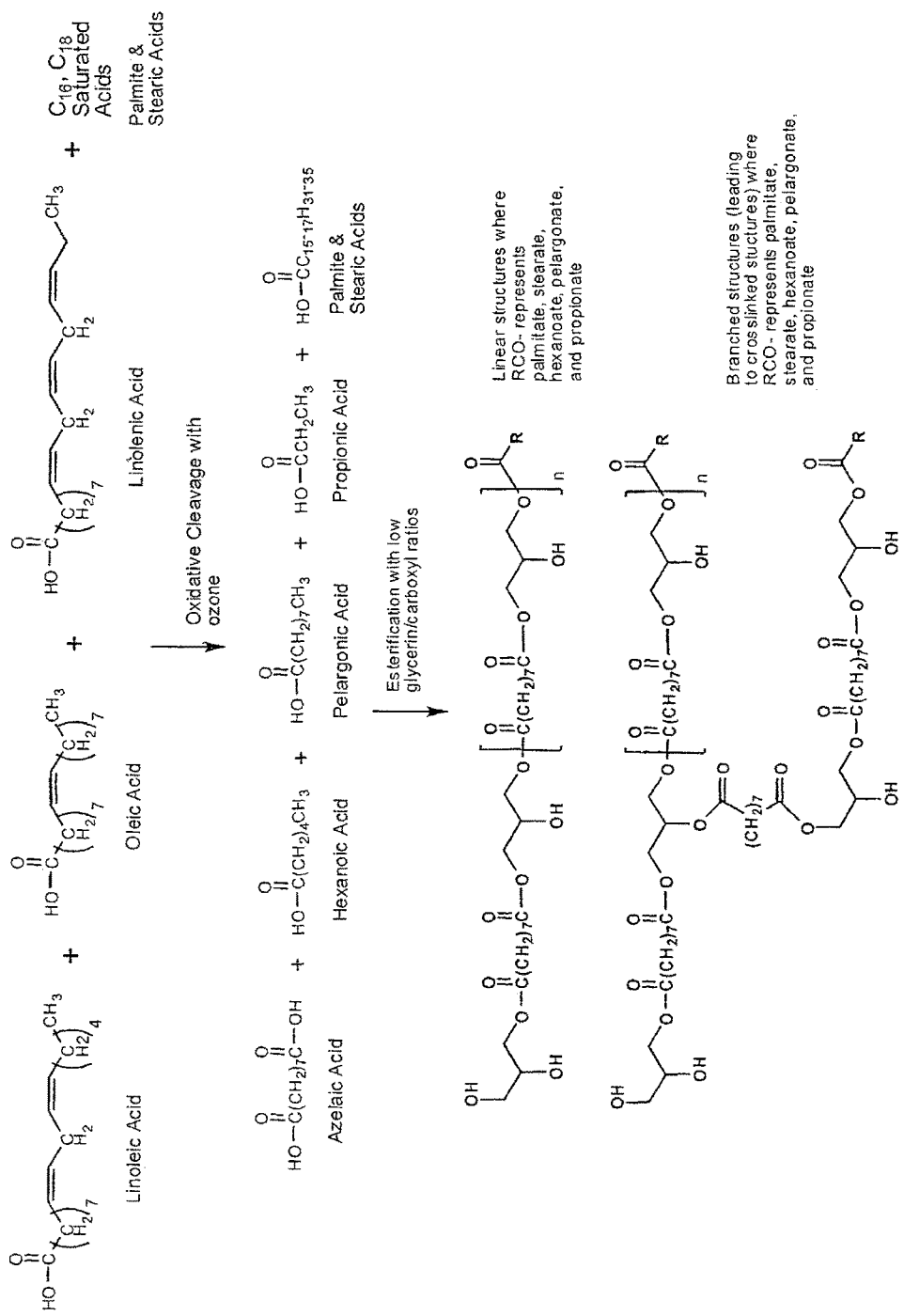
FIG. 2 is a schematic of the ester polyols formed from the esterification of ozone acids with glycerin under relatively low hydroxyl/carboxyl ratios.

FIG. 2 shows the production of ozone acids from fatty acids by oxidative ozonolysis with glycerin under relative low glycerin to ozone acids ratios. When this mixture of ozone acids is esterified with glycerin under relatively low glycerin concentrations, the major glyceride products (ester polyols) are diglycerides and triglycerides, as shown. The ester polyols have extended molecular weights compared to the structures sown in FIG. 1 and also the monofunctional carboxylic acids (palmitic, stearic, hexanoic, pelargonic, and propionic acids) serve to cap some of the glyceride hydroxyl groups. Another feature of the ester polyol of FIG. 2 is the crosslinking via difunctional Azelaic acid moieties, as shown in the lower ester polyol branched structure of FIG. 2.

The ester polyols of FIG. 2 generally have lower hydroxyl values (HV) that qualifies them as polyols useful for polyurethane flexible foams and coatings. The range and relative concentrations of the structures that will be obtained at varying glycerin to ozone acid concentrations can be predicted by molecular modeling.

In the present invention, the ester polyols have an additional unique structural aspect due to their incorporation of branched primary polyols. The branched primary polyols are effective in reducing and/or inhibiting phase separation in hydrocarbon chains, particularly from palm feedstock because palm feedstock contains high amounts of saturated fatty acids that cause phase separation. An example of a branched primary polyol is Trimethylolpropane (TMP) that is shown below.

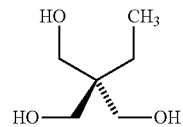

Branched primary polyols may be selected from 1,2-propanediol; 2-methyl-1,3-propanediol (2-MePG); trimethylolpropane (TMP); di-trimethylolpropane (Di-TMP); neopentyl glycol (NPG); pentaerythritol (PE); and dipentaerythritol (diPE).

Specifically, the ester polyol may have a repeated group $(RCO_2R')$ where R represents palmitate, stearate, hexanoate, pelargonate, propionate and azelate (as di-esters derived from the ozone acids, as shown in FIGS. 1 and 2. R' is derived from the primary polyol structure.

In an embodiment, the ester polyols may be linear structures. In another embodiment, the polyol esters may be branched structures. Both may incorporate at least one branched polyol. The structure of the branched polyol esters hinders the close packing of hydrocarbon chains, which inhibits crystallization.

In all polyols, the presence of hydroxyl functionality and the selection of hydroxyl to carboxyl ratio (HCR) are responsible for excess hydroxyl content or hydroxyl value (HV) of the product polyol. This is achieved by the relative amounts of primary polyol and the amounts of carboxylic acid group containing compounds, both diacids and monoacids, in the polyol synthesis. Thus, the higher the amount of primary polyol, the higher the resulting hydroxyl value (HV) of the product polyol. The versatility of the polyol process is a key feature in being able to develop biopolyols which span a range of properties and characteristics and allowing use in different applications. For example, rigid foam polyols typically have hydroxyl values (HV) in the 250-450 KOH/g range and also possess some crosslinking to provide rigidity. Flexible foam polyols typically have hydroxyl values (HV) in the 50-150 KOH/g range. Coating polyols typically have hydroxyl values (HV) in the 150-250 range.

These characteristics are also attainable by selecting the input compounds and adjusting their Difunctional Monofunctional ratio (DMR) and hydroxyl/carboxyl ratio (HCR).

The difunctional/monofunctional ratio (DMR) is the ratio of the molar amount of diacid to monoacids in the ozone acid or ozone acid mixtures. The use of a higher difunctional/monofunctional ratio (DMR) results in increased ester polyol r viscosities and decreased volatilities. Conversely, a decreased difunctional/monofunctional ratio (DMR) results in decreased ester polyol component molecular weights, resulting in decreased viscosities and increased volatilities of the ester polyols.

FIG. 3 shows the optimal structures formed from the esterification reaction of ozone acids with primary polyols. The two ratios, difunctional to monofunctional acid ratio (DMR) and hydroxyl to carboxyl ratio (HCR) dictate the structure of ester polyols. The combination of these specific ratios establishes the key parameters and therefore where the applications can be used. In broad terms, the three most important application areas, such as, lubricant base stock, polyurethane rigid foam, and/or flexible foam can be represented on the two-axis plot, as shown in FIG. 3.

The difunctional to monofunctional acid ratio (DMR) is considered a key control parameter in the production of polyol esters. It is generally constrained by the latent difunctional carboxylic acid components of the feedstock that result directly from the ozonolysis of the unsaturated fatty acids with the principal diacid formed being Azelaic acid. The maximum theoretical DMR of the fatty acid composition of fractionated PFAD is 0.71. For comparison, the DMR of soybean oil fatty acids has a value of 1.51 due to the increased level of unsaturation. The difunctional to monofunctional acid ratio (DMR) of PFAD can be adjusted downward by the additional monoacid, as illustrated in FIG. 3, to access compositional ranges of a polyol which suits the lubricant base stock. The presence of increased amounts of azelaic acid favors the formation of higher chain extended structures.

In all polyols, the presence of hydroxyl functionality and the selection of hydroxyl/carboxyl ratio (HCR) are responsible for excess hydroxyl content or hydroxyl value (HV) of the product polyol. This is achieved by the relative amounts of primary polyol and the amounts of carboxylic acid group containing compounds, both diacids and monoacids, in the polyol synthesis. Thus, the higher the amount of primary polyol, the higher the resulting hydroxyl value (HV) of the product polyol.

In combination, difunctional to monofunctional acid ratio (DMR) and hydroxyl/carboxyl ratio (HCR) for a given feedstock, choice of primary polyol, and additional monoacid can be used to produce a wide range of polyols with varying structure and hydroxyl value (HV).

In all polyols, the presence of hydroxyl functionality and the selection of hydroxyl to carboxyl ratio (HCR) are responsible for the hydroxyl value (HV) of the product polyol. This is achieved by the amounts of primary polyol and carboxylic acid group, both diacids and monoacids, used in the polyol synthesis. Thus, the higher the amount of primary polyol, the higher the resulting hydroxyl value (HV) of the product.

Table A lists the fatty acids and weight percentages of fractionated PFAD that were then subjected to simulated oxidative ozonolysis to produce a mixture of ozone acids as shown with their individual calculated weight percentages (% wt).

TABLE A

|  | % wt |
|---|---|
| Fractionated PFAD | |
| Oleic | 68.98 |
| Linoleic | 12.85 |
| Linolenic | 2.76 |
| Palmitate | 11.11 |
| Stearate | 3.19 |
| Myristic | 0.16 |
| Arachidic | 0.86 |
| Behenic | 0.08 |
| Total | 99.99 |
| Ozone acids | |
| Azelaic | 46.86 |
| Acetic | 3.27 |
| Hexanoic | 4.42 |
| Nonanoic | 32.07 |
| Propionic | 0.61 |
| Palmitic | 9.22 |
| Stearic | 2.65 |
| Myristic | 0.13 |
| Arachidic | 0.71 |
| Behenic | 0.07 |
| Total | 100.00 |

Table B lists the fatty acids and weight percentages of fatty acids expected from high oleic soybean oil that were then subjected to simulated oxidative ozonolysis to produce a mixture of ozone acids as shown with their weight percentages (% wt).

TABLE B

|  | % wt |
|---|---|
| High Oleic Fatty Acid Mixtures | |
| Oleic | 75.64 |
| Linoleic | 11.35 |
| Linolenic | 0.59 |
| Palmitic | 4.41 |
| Stearic | 2.83 |
| Myristic | 0.43 |
| Lauric | 4.53 |
| Arachidic | 0.22 |
| Total | 100.00 |
| Ozone acids | |
| Azelaic | 49.38 |
| Acetic | 2.22 |
| Hexanoic | 3.89 |
| Nonanoic | 35.09 |
| Propionic | 0.13 |
| Palmitic | 3.65 |
| Stearic | 2.34 |
| Myristic | 0.36 |
| Lauric | 3.75 |
| Arachidic | 0.18 |
| Total | 100.00 |

The targeted hydroxyl value (HV) range of ester polyols used to formulate rigid polyurethane foam is 250-450 mg KOH/g. Therefore, primary polyols having a high number of hydroxyl groups per molecule, such as glycerin and sorbitol, were incorporated to increase the hydroxyl value and cross-linking potential. The base calculation to determine the formulation to produce ester polyols for various foam applications is the hydroxyl to carboxylic acid (OH:COOH) ratio.

According to another aspect of the invention, there is also provided a method of making a "rigid" foam, comprising the sequential steps of:
  reacting at least one mixture of ozone acids, the mixture of ozone acid(s) having at least one hydroxyl group and at least one carboxyl group, a ratio of the at least one hydroxyl group to the at least one carboxyl group is a hydroxyl/carboxyl ratio;
  esterifying the mixture of ozone acid(s) with at least one primary polyol to produce an ester polyol according to the invention;
  esterifying the ester polyol with at least one carboxylic acid to produce at least one ester polyol ester; and
  reacting the ester polyol ester with at least one petroleum polyol, at least one cross-linking agent, cell opening additives, and at least one isocyanates to produce foam.

According to another aspect of the invention, there is also provided a method of making a "flexible" foam, comprising the sequential steps of:
  reacting at least one ozone acid, the ozone acid(s) having at least one hydroxyl group and at least one carboxyl group, a ratio of the at least one hydroxyl group to the at least one carboxyl group is a hydroxyl/carboxyl ratio;
  esterifying the ozone acid(s) with at least one primary polyol to produce an ester polyol according to the invention;
  esterifying the ester polyol with at least one carboxylic acid to produce at least one ester polyol ester; and
  reacting the ester polyol ester with at least one petroleum polyol, at least one cell opening additive, and at least one isocyanate to produce foam.

Accordingly, there is also provided an ester polyol, wherein the ester polyol comprises the reaction product of:
  at least one ozone acid; and
  at least one branched primary polyol.

The ester polyol ester according to the invention comprises the structure

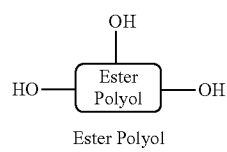

Ester Polyol

The branched primary polyol may be selected from 2-methyl-1,3-propanediol (2-MePG); trimethylolpropane (TMP); di-trimethylolpropane (Di-TMP); pentaerythritol (PE); dipentaerythritol diPE); neopentyl glycol (NPG); and a mixture thereof. In particular, the branched primary polyol(s) is selected from 2-methyl-1,3-propanediol (2-MePG); trimethylolpropane (TMP); di-trimethylolpropane (Di-TMP); neopentyl glycol (NPG) and a mixture thereof. More in particular, the branched primary polyol comprises trimethylolpropane (TMP). More in particular, the at least one branched primary polyol comprises adding a mixture of at least two branched primary polyols, for example, 2-methyl-1,3-propanediol (2-MePG) and trimethylolpropane (TMP).

The ester polyol according to the invention may be one or more ester polyol having the formula of:

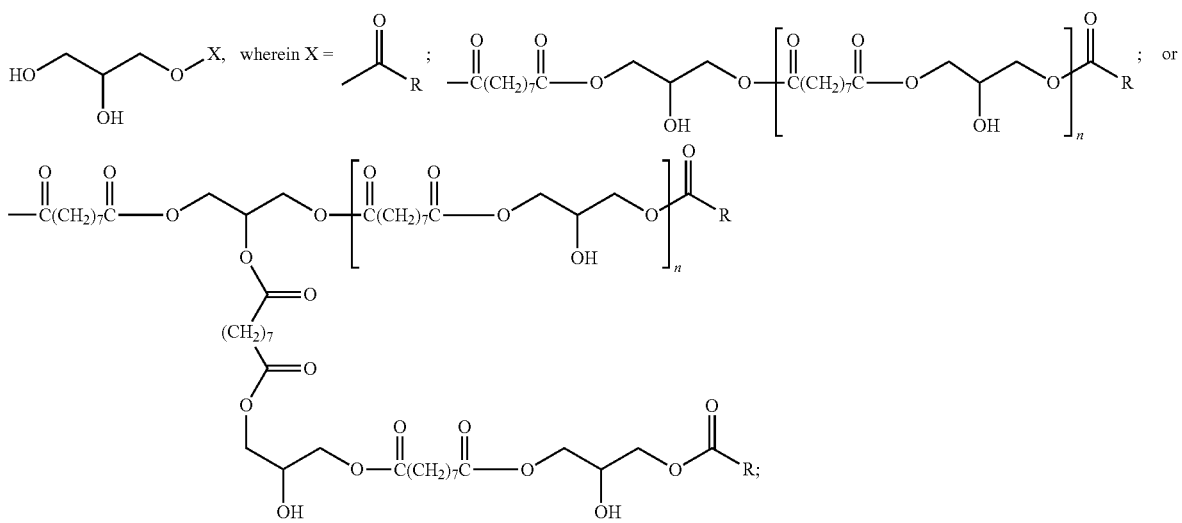

and
  R is selected from palmitate, stearate, hexanoate, pelargonate, propionate monoesters and azelate diesters, wherein n is from 1 to 3.

The ester polyol according to the invention may have a hydroxyl value (HV) from about 20 (mg KOH/g) to about 450 (mg KOH/g).

According to another aspect, there is also provided an ester polyol ester obtainable or obtained according to any method of the invention. The ester polyol ester according to any aspect of the invention comprises the structure:

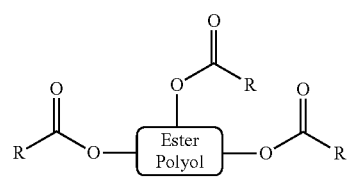

There is also provided a foam obtained or obtainable according to any method of the invention. In particular, there is provided a foam, wherein the foam is prepared from an ester polyol and/or an ester polyol ester according to the invention.

In particular, there is provided a foam, wherein the foam comprises the reaction product of:
  at least one ozone acid; and
  at least one branched primary polyol.

The foam may be a rigid or flexible foam.

The foam according to the invention may have a tensile strength measured from about 7.75 (psi) to about 36.9 (psi). In particular, from about 9.7 (psi) to about 36.9 (psi). In particular, from about 9.7 (psi) to about 13.5 (psi). More in particular, from about 9.7 (psi) to about 11.55 (psi). Even more in particular, from about 7.75 (psi) to about 11.55 (psi).

The foam according to any aspect of the invention, may comprise an ester polyol according to any aspect of the invention in an amount of about 10% to about 100% and the petroleum polyol is an amount of about 90% to about 0%. In particular, the ester polyol is in an amount of about 10% and the petroleum polyol component is in an amount of about 90%. Alternatively, the ester polyol is in an amount of about 20% and the petroleum polyol component is in an amount of about 80%. %. Alternatively, the ester polyol is in an amount of about 100% and the petroleum polyol component is in an amount of about 0%. Alternatively, the ester polyol is in an amount of about 50% and the petroleum polyol component is in an amount of about 50%. %. Alternatively, the ester polyol is in an amount of about 90% and the petroleum polyol component is in an amount of about 10%.

In preparing the foam of the invention, the polyol may have a hydroxyl value (HV) from about 20 (mg KOH/g) to about 450 (mg KOH/g). In particular, from about 250 (mg KOH/g) to about 400 (mg KOH/g). Alternatively, wherein the ester polyol has a hydroxyl value (HV) ranging from about 50 (mg KOH/g) to about 150 (mg KOH/g).

The foam of the invention may have a free rise density from about 2.1 (pcf) to 2.6 (pcf). In particular, from about 2.1 (pcf) to about 2.3 (pcf). Alternatively, from about 2.3 (pcf) to about 2.6 (pcf).

The foam according to any aspect of the invention may have a density of about 2.4 (pcf) to about 2.5 (pcf).

The foam according to any aspect of the invention may have a thermal conductivity (K-factor) of about 0.148 to about 0.154.

The foam according to any aspect of the invention may have a maximum load of about 5.50% to 6.25%.

The foam according to any aspect of the invention may have an elongation at a break measured at about 78.3% to about 118.5%.

The foam according to any aspect of the invention may have a resiliency of about 23.1 to 59.0%.

The foam according to any aspect of the invention may have a ball Resilience (16 mm) with a Rebound percentage of about 23.1% to about 59.0%.

The foam according to any aspect of the invention may comprise at least one compound selected from an petroleum polyol, a cross-linking agent, a cell opening additive and an isocyanate, or a mixture thereof. In particular, the foam may comprises at least one cell opening additive and at least one isocyanate.

The foam according to any aspect of the invention may comprise at least one cross-linking agent comprising at least one branched primary polyol selected from 2-methyl-1,3-propanediol (2-MePG); trimethylolpropane (TMP); di-trimethylolpropane (Di-TMP); pentaerythritol (PE); dipentaerythritol diPE); neopentyl glycol (NPG); and at least one isocyanate, or a mixture thereof. In particular, the foam may comprise at least one branched primary polyol(s) is selected from 2-methyl-1,3-propanediol (2-MePG); trimethylolpropane (TMP); di-trimethylolpropane (Di-TMP); neopentyl glycol (NPG) and a mixture thereof. The at least one branched primary polyol may comprise trimethylolpropane (TMP). The foam of the invention may comprise at least two branched primary polyols, for example 2-methyl-1,3-propanediol (2-MePG) and trimethylolpropane (TMP).

According to another aspect of the invention, there is also provided a polyurethane coating, prepared using the ester polyol according to any aspect of the invention.

According to another aspect of the invention, there is provided a method of reducing the separation of a composition comprising at least one ester polyol in a single phase into two or more phases, the method comprising esterifying at least one ozone acid with at least one branched primary polyol to produce the at least one ester polyol, thereby reducing the phase separation of the at least one ester polyol. In particular, the composition may be in a single liquid phase. According to a particular aspect, the at least one ester polyol does not substantially separate into more than one phase. Further, the method of the invention also comprises allowing the composition to achieve to the temperature range from about 20° C. to about 80° C.

Having now generally described the invention, the same will be more readily understood through reference to the following examples which are provided by way of illustration, and are not intended to be limiting of the present invention.

EXAMPLES

Example 1

Preparation of a Palm-Based Rigid Foam Polyol

To produce palm-based rigid foam polyol, 80.36 g of azelaic acid, 3.69 g of acetic acid, 6.46 g of hexanoic acid, 58.29 g of nonanoic acid, 0.22 g of propionic acid, 6.06 g of palmitic acid, 4.15 g of stearic acid, 0.6 g of myristic acid, 6.23 g of lauric acid, 69.03 g of glycerin, 41.22 g of sorbitol and 0.17 g of tin (II) oxalate were weighed into a 500 ml three neck round bottom flask. The mixture was stirred using an overhead stirrer and heated to 180° C. to ensure all components dissolved and homogenized. The temperature was then increased to 215° C.-220° C. and the byproduct water was collected throughout the reaction. The reaction was monitored by measuring acid value (AV) and was considered complete when the AV reached below 3 mg KOH/g. The resultant polyol (labeled 53144-09-10) had a hydroxyl value (HV) of 378.8 mg KOH/g and AV of 1.04 mgKOH/g. The final product was a clear liquid.

Rigid Foam Polyols

Preparation of Palm-Based Polyurethane Rigid Foam Samples

Table C lists the typical components used to prepare rigid polyurethane sample. For comparison, the conventional sucrose-based polyol Jeffol SG-360 is also used to make polyurethane foam sample using the same formulation. Foams were prepared at an isocyanate index of 105 with biobased polyol 53144-09-10 as a sole polyol and as 50% replacement of Jeffol SG 360 polyol with and without addition of 10% glycerin as crosslinker. Water in combination with Enovate 3000 (HFC-245fa) was used as a blowing agent.

In order to balance the foaming profile, the amount of Dabco 33LV was reduced and the amount of Niax A1 was increased in formulations based on palm-based polyol 53144-09-10 in comparison to the reference formulation based on sucrose-based polyol Jeffol SG-360 as shown in Table D. Dabco 33LV performs as both "blowing" and "gelling" catalyst. The additive Niax A1 is a very strong "blowing" catalyst.

TABLE C

Rigid Foam Formulation Components

| Designation | Materials Type |
|---|---|
| POLYOLS | |
| 52926-37-15 | Hydroxyl Value = 400; Acidity Value = 0.9 |
| 52926-33-14 | Hydroxyl Value = 520; Acidity Value = — |
| 52926-35-26 | Hydroxyl Value = 406; Acidity Value = 2.1 |
| Jeffol SG-360 (comparative) | Sucrose/glycerin-based polyol; Hydroxyl value = 360 (Eq. wt. = 153.7) |
| CROSSLINKER | |
| Superol V Glycerin | 1,2,3-Propanetriol; (Eq. wt = 30.67) |
| SURFACTANT | |
| Dabco DC193 | Polysiloxane |

TABLE C-continued

Rigid Foam Formulation Components

| Designation | Materials Type |
|---|---|
| CATALYSTS | |
| Dabco 33LV | 33% Triethylene diamine in dipropylene glycol |
| Dabco T-12 | Dibutyltin dilaurate |
| Niax A1 | bis(2-dimethylaminoethyl) ether |
| ISOCYANATE | |
| Rubinate M | Polymeric MDI; Functionality = 2.7; Eq. wt = 135.05 |

All rigid foams were prepared using a standard laboratory high-torque mixer. The polyol component and isocyanate component were mixed for 10 seconds. Afterwards, the mixture was transferred into an open cake box before the cream time. Foaming profile, including cream time, gel time, rise time, and tack-free time was measured on all foams. The performance of both foams using Jeffol SG-360 and polyol 53144-09-10 is summarized as in the Table D.

The biopolyol exhibited similar reaction profile times (cream, gel and rise) as well as densities at both the 50% and 100% replacement levels of the petroleum polyol.

After aging at room conditions for one week, the foams were cut and tested for density according to ASTM D 1622-03 and apparent dimensional stability by aging at 120° C. for 60 minutes (in-house procedure for screening foam dimensional stability). The dimensional stability of the biopolyol foams without glycerine was satisfactory.

TABLE D

Example of formulations for polyurethane rigid foam at 0%, 50% and 100% replacement and their performance profiles. Formulations and properties of rigid polyurethane foams based on biobased polyol 53144-09-10[a]

| Components | Eqv. Weight | 100% Conventional Polyol | 50% Replacement | 100% Replacement | 50% Replacement with Added Glycerin | 100% Replacement with Added Glycerin |
|---|---|---|---|---|---|---|
| Polyol System | | | | | | |
| Jeffol SG-360 | 153.7 | 100 | 50 | 0 | 45 | 0 |
| 53144-09-10 | 148.1 | 0 | 50 | 100 | 45 | 90 |
| Superol V Glycerin (Crosslinker) | 30.67 | 0 | 0 | 0 | 10 | 10 |
| Water | 9 | 2 | 2 | 2 | 2 | 2 |
| Dabco DC193 (Surfactant) | 748 | 2.5 | 2.5 | 2.5 | 2.5 | 2.5 |
| Dabco 33LV (Amine catalyst) | 105 | 1.0 | 0.6 | 0.6 | 0.6 | 0.6 |
| Niax A-1 | 233.7 | 0.2 | 0.4 | 0.5 | 0.4 | 0.5 |
| Isocyanate System | | | | | | |
| Rubinate M (Polymeric MDI) | 134.6 | 125.31 | 126.6 | 128.4 | 163.3 | 164.9 |
| Isocyanate Index | | 105 | 105 | 105 | 105 | 105 |
| Reaction Profile of Free-rise Foams | | | | | | |
| Mix time, sec. | | 10 | 10 | 10 | 10 | 10 |
| Cream time, sec. | | 16 | 19 | 25 | 22 | 40 |
| Gel time, sec. | | 110 | 123 | 135 | 160 | 180 |
| Rise time, sec. | | 187 | 180 | 215 | 230 | 240 |
| Tack-free time, sec. | | 220 | 210 | 200 | 215 | 230 |
| Properties of Screening Foams[a] | | | | | | |
| Free-rise density, pcf | | 2.2 | 2.1 | 2.3 | 2.2 | 2.2 |
| Apparent Dimensional | | Hard; No deformation; | Hard; No deformation; | Hard; No deformation; | Hard; No deformation; | Hard; No deformation; |

TABLE D-continued

Example of formulations for polyurethane rigid foam at 0%, 50% and 100% replacement and their performance profiles. Formulations and properties of rigid polyurethane foams based on biobased polyol 53144-09-10[a]

| Components | Eqv. Weight | 100% Conventional Polyol | 50% Replacement | 100% Replacement | 50% Replacement with Added Glycerin | 100% Replacement with Added Glycerin |
|---|---|---|---|---|---|---|
| Stability @ 120° C. for 30 min. | | No shrinkage | No shrinkage | No shrinkage | No shrinkage | No shrinkage |
| Properties of Foams Prepared for K-Factor Measurement[b] | | | | | | |
| Density, pcf | | 2.4 ± 0.03 | 2.5 ± 0.09 | 2.4 ± 0.05 | — | — |
| Thermal Conductivity K-factor | | 0.148 ± 0.002 | 0.153 ± 0.008 | 0.154 ± 0.017 | — | — |

[a]A total of 50 grams of polyol was used in each screening experiment. Foams for K-factor testing were prepared with total of 250 grams of polyol using a paper box of 3" × 18" × 12¼"size.

An advantage of the ester polyol intermediate in the present invention is that it can replace up to 100% petroleum polyol at the same level of performance. As shown in Table D, high hydroxyl biopolyols of the present invention can replace the petroleum polyol component in a rigid foam formulation. The hydroxyl value of the comparative polyol, Jeffol SG-360, is 365 and for Polyol 53144-09-10 is 378.8. Jeffol SG-360 will be used as a comparative example when formulating foams of the present invention. The amount of Polyol 53144-09-10 that was used to replace petroleum polyol ranges 45%-100%. This was accomplished either with solely the biopolyol or in combination with a small amount glycerin which served to increase the mechanical stiffness of the foam.

Glycerin is viewed as an acceptable additive since it is also biobased, however, it can result in brittle and friable foam when used in larger amounts. Trials conducted did not require any additional glycerin and demonstrated an incremental improvement in the overall polyol development. Subsequent thermal insulation testing also showed that rigid foams formulated with the palm based biopolyols were comparable to the petroleum reference foams and is therefore suitable for insulation applications.

Thermal insulation is a key application for rigid polyurethane foams and therefore it was essential to determine if the biobased polyols would meet critical property requirements. A list of raw materials used in this evaluation is shown in Table E.

TABLE E

Rigid Foam Formulation Components for Insulation Tests

| Designation | Materials Type |
|---|---|
| POLYOLS | |
| 53144-09-10 | Hydroxyl Value = 378.8; Acidity Value = 1.04 Palm-based polyol |
| Jeffol SG-360 | Sucrose/glycerin-based polyol; Hydroxyl value = 365 (Eq. wt. = 153.7) |
| CROSSLINKERS | |
| Superol V Glycerin | 1,2,3-Propanetriol; (Eq. wt = 30.67) |
| SURFACTANTS | |
| Dabco DC193 | Polysiloxane |

TABLE E-continued

Rigid Foam Formulation Components for Insulation Tests

| Designation | Materials Type |
|---|---|
| CATALYSTS | |
| Dabco 33LV | 33% Triethylene diamine in dipropylene glycol |
| Dabco T-12 | Dibutyltin dilaurate |
| ISOCYANATES | |
| Rubinate M | Polymeric MDI; Functionality = 2.7; Eq. wt = 134.61 |

Foams for K-factor measurements were prepared using the same hand-mixing procedure by pouring foaming mixture into a paper box of 3"×18"×12¼" dimensions. Foams were cut for K-factor measurement after aging for 11 days at room conditions. K-factor measurement was carried out 24 hours after cutting the samples with 12"×12"×1" dimensions. The measurements were carried out on Thermal Conductivity Analyzer ANACON, Model TCA-12 according to ASTM C 518-02. Standard Reference Material 1450c (Fibrous Glass Board) provided by National Institute of Standards and Technology was used for calibration of the thermal conductivity analyzer.

A temperature of the cold plate was set to 50° F. and temperature of the hot plate to 100° F. for K-factor measurement. The properties of the foam are also summarized in Table D. The apparent cell structure of foams based on biobased polyol 53144-09-10 was similar to the reference foams (FIGS. 4 and 5). All foams exhibited somewhat higher density than targeted 2 pcf. All foams prepared including foams based on 50% and 100% biobased polyol 53144-09-10 and prepared without glycerol, exhibited good dimensional stability in exposure to 120° C. for 60 minutes (FIG. 6).

Thermal conductivity measurements were carried out on foam prepared without any glycerin. K-factors of foams based on palm-based based polyol was similar to that of the reference foams, indicating that conventional sucrose-based polyether polyol for rigid foams can be replaced with biobased polyol 53144-09-10 in rigid foam formulations targeting thermal insulation properties.

The resulting K-factors of 0.148 Btu-in/hr-ft$^{2\circ}$ F. measured for reference foams and 0.153-0.154 Btu-in/hr-ft$^{2\circ}$ F. measured for foams based on biobased polyol are in the range reported for foams with the same density range prepared with similar levels of HFC-245fa.

All foams exhibited somewhat higher density than targeted 2 pcf. Foams were prepared using laboratory hand-mixing equipment, which is not best suited to control the amount of volatile Enovate 3000 in the blend.

All foams prepared in screening experiments, including foams based on 50% and 100% biobased polyol 53144-09-10 prepared without glycerol, and exhibited good dimensional stability in exposure to 120° C. for 60 minutes, as shown in FIG. 4 as RP-1, B50, and B100.

FIG. 5 shows photographs of rigid foam samples prepared for formulation screening with glycerol. In FIG. 5, the foam samples are labeled as RP-1 (comparative example) and experimental examples, B500, and B100G FIG. 6 shows photographs of rigid foam samples (with and without glycerol) prepared for formulation screening after heating at 120° C. for 60 minutes. FIG. 6 shows comparative example RP-1 and experimental examples, B50, and B100, B50G, and B100G.

Flexible Foam Polyol

As of yet, there are no biobased polyols which can be formulated at a 100% level to produce a high resilience foam typical of the consumer products uses such as furniture and bedding. A significant amount of petroleum polyol, typically in excess of 70 wt % of the polyol, is currently required to achieve critical performance characteristics such as resilience with current commercial biopolyols. Improvements were made to increase the biopolyol content of flexible foams while maintaining performance characteristics. Several compositions were examined and compared with a conventional petroleum polyol formulation. These unoptimized formulations and results show potential for increased biopolyol content with the palm based polyols have a low hydroxyl value (HV). The method of preparation of ester polyols intermediates for flexible foam is similar as rigid foam but at a different hydroxyl:carboxyl (OH/COOH) ratio, which is between 1.05 to 1.15. Flexible foam polyols typically have hydroxyl values (HV) in the 50-150 mg KOH/g range. The lowest HV polyols produced by ozone-based processes will typically be used for flexible foams. The decreased starting material hydroxyl/carboxyl ratio of 1.10 used in these flexible foam candidates was expected to provide even lower hydroxyl values compared to the rigid foam and coating polyols while also providing higher molecular weights polyols.

Example 2

Preparation of Palm-Based Flexible Foam Polyol

To produce palm-based flexible polyurethane foam polyol, 361.62 g of azelaic acid, 16.62 g of acetic acid, 29.07 g of hexanoic acid, 332.88 g of nonanoic acid, 0.99 g of propionic acid, 27.27 g of palmitic acid, 18.66 g of stearic acid, 2.70 g of myristic acid, 28.05 g of lauric acid, 195 g of glycerin, 35.01 g of 2-methyl-1,3-propanediol and 0.63 g of tin(II)oxalate were weighed in a 1 L three neck round bottom flask. The mixture was stirred using an overhead stirrer and heated to 180° C. to ensure all components were dissolved and homogenized. The temperature was then increased to 210° C.-215° C. and the byproduct water was collected throughout the reaction. The reaction was monitored by acid value (AV) and was considered complete when the AV reaches below 3 mg KOH/g. The resultant polyol (labeled 53045-13-10) had an HV of 23.2 mg KOH/g and an AV of 0. The final product was a clear liquid.

Preparation of Polyurethane Flexible Foam Samples

The ingredients as listed in the following Table F were used to prepare flexible polyurethane foam sample. For comparison, the conventional petroleum based polyol Jeffol G31-28 was also used to make polyurethane foam sample. Foams were prepared at an isocyanate index of 90 with 10%, 30% and 50% replacement of Jeffol G31-28 with biobased polyol. Other components used were water, Lumulse POE 26 as the cell opener, Tegostab B 4690 as the surfactant, and Dabco 33LV, diethanolamine as crosslinker and Niax A-1 as the blowing catalyst. The isocyanate system was a single system and used Mondur MRS-2. Both formulations and the properties of resultant foams are summarized in Table F.

TABLE F

| Flexible Foam Formulation Components | |
|---|---|
| Designation | Materials Type |
| POLYOLS | |
| 52962-24-29 | Hydroxyl Value = 82.37 |
| | Acidity Value = 1.10 |
| 52962-26-21 | Hydroxyl Value = 64.74 |
| | Acidity Value = 1.38 |
| Jeffol G 31-28 | Polyether triol (Eq. wt. = 1961.5) |
| SURFACTANTS | |
| Tegostab B 4690 | Polyether/Silicone Oil Mix |
| | Eq. Wt. = 1335.7 |
| Tegostab B 4113 | Polyether/Silicone Oil Mix |
| | Eq. Wt. = 1304.6 |
| CELL OPENER | |
| Lumulse POE 26 | Eq. Wt = 416.2 |
| CROSS-LINKER | |
| Diethanol amine | 99% Diethanol amine; Eq. Wt. = 35 |
| CATALYSTS | |
| Dabco 33LV | 33% Triethylene diamine in dipropylene glycol |
| Dabco T-12 | Dibutyltin dilaurate |
| DMEA | Dimethylethanolamine |
| Niax A1 | bis(2-dimethylaminoethyl) ether |
| ISOCYANATES | |
| Mondur MRS-2 | 2,4' rich diphenylmethane diisocyanate (F = 2.2; Eq. wt. = 130.03) |
| Rubinate 1680 | Uretonimine modified MDI (F = 2.12; Eq. wt. = 140.0) |

TABLE G

Flexible Foam Formulations and Properties
Formulations and properties of flexible polyurethane foams based on palm-based polyol 53045-13-10

| Components | Equivalent Weight | 100% Petroleum Based 0% Replacement | Equivalent Recipe 50% Replacement | Recipes with Lower Amount of Cell Opener | | Recipes with Higher Amount of Cell Opener | |
|---|---|---|---|---|---|---|---|
| | | | | 10% Replacement | 30% Replacement | 10% Replacement | 50% Replacement |
| Petroleum Based Jeffol G31-28 | 1961.54 | 97 | 48.5 | 89.1 | 69.3 | 85.5 | 47.5 |
| Palm based polyol 53045-13-10 | 2418.10 | 0 | 48.5 | 9.9 | 29.7 | 9.5 | 47.5 |
| % Replacement | | 0 | 50 | 10 | 30 | 10 | 50 |
| Water | 9 | 3.6 | 3.6 | 3.6 | 3.6 | 3.6 | 3.6 |
| Lumulse POE 26 (Cell Opener) | 416.2 | 3 | 3 | 1 | 1 | 5 | 5 |
| Niax I-670 (Cell Opener) | 217.4 | 0 | 0 | 0 | 0 | 0 | 0 |
| Tegostab B 4690 (Surfactant) | 1335.7 | 1 | 1 | 1 | 1 | 1 | 1 |
| Dabco 33LV (Amine catalysts) | 105 | 0.8 | 0.8 | 0.8 | 0.8 | 0.8 | 0.8 |
| Diethanolamine (Crosslinking agent) | 35.04 | 1 | 1 | 1 | 1 | 1 | 1 |
| Niax A-1 (Blowing catalyst) | 233.7 | 0.1 | 0.1 | 0.1 | 0.1 | 0.1 | 0.1 |
| Isocyanate System | | | | | | | |
| Mondur MRS-2 (Polymeric MDI) | 130.03 | 57.81 | 57.26 | 57.26 | 57.03 | 58.15 | 57.72 |
| Isocyanate Index | | 90 | 90 | 90 | 90 | 90 | 90 |
| Foam Properties Rise Profile (sec) | | | | | | | |
| Cream Time | | 9 | 16 | 15 | 15 | 15 | 20 |
| Gel Time | | 45 | 65 | 50 | 52 | 50 | 75 |
| Rise Time | | 80 | 80 | 85 | 80 | 70 | 100 |
| Resilience Rebound (%) | | 62 | 41 | 54 | 47 | 61 | 41 |
| Density (pcf) | | 2.78 | 2.75 | 2.48 | 2.56 | 2.78 | 2.57 |
| Tensile Strength (psi) | | 11.55 | 10.68 | 10.28 | 10.58 | 10.11 | 7.75 |
| Elongation at Break (%) | | 253.82 | 169.8 | 270.88 | 247.28 | 228.58 | 176.22 |

As shown in Table G, the biobased polyol (53045-13-10) managed to replace petroleum based polyol up to 50% and still meet the resilient property of minimum of 40% to be used in high resilient foam applications. Other properties such as tensile strength and elongation at break are comparable to the petroleum based polyol at up to 30% replacement. At 50% replacement, the tensile strength and elongation at break were lower than 100% petroleum based polyol.

Coating Polyols

Coating polyols typically have hydroxyl values (HVs) in the 150-250 mg KOH/g range and may possess some crosslinking to provide enhanced hardness. The decreased starting material hydroxyl/carboxyl ratio of 1.58 was expected to provide lower hydroxyl values compared to the rigid foam polyol and also provide a higher molecular weight based on well-known polymerization principles.

Example 3

Preparation of Palm-Based Polyurethane Coating Polyol

To produce palm-based polyurethane coating polyol, 62.95 g of azelaic acid, 3.55 g of acetic acid, 30.25 g of hexanoic acid, 42.13 g of nonanoic acid, 0.33 g of propionic acid, 13.6 g of palmitic acid, 1.6 g of stearic acid, 1.6 g of myristic acid, 68.5 g of trimethylolpropane (branched primary polyol), 25.5 g of 2-methyl-1,3-propanediol and 0.15 g of tin(II)oxalate were weighed in a 500 mL three neck round bottom flask. The mixture was stirred using an overhead stirrer and heated to 180° C. to ensure all components had dissolved and homogenized. The temperature was then increased to 210° C.-215° C. and the byproduct water was collected throughout the reaction. The reaction was monitored by acid value (AV) and was considered complete when the AV reached below 3 mg KOH/g. The resultant polyol (labeled 52781-32-30) had an HV of 207 mg KOH/g and an AV of 0.0. The final product was a clear liquid.

TABLE H

Properties of Palm-based Polyurethane Coating Sample

| Properties | Value |
|---|---|
| Acid Value (mgKOH/g) | 0.0 |
| Hydroxyl Value (mgKOH/g) | 207.0 |
| Molecular Weight (g/mol) | 1065 |
| Viscosity (cPs @ 40° C.) | 161.8 |
| Appearance | Clear Liquid |
| Hardness level (Pencil test) | H Hardness |

The polyurethane foams and coatings of the present invention are formed by the reaction of an isocyanate, a cross-linking agent, cell opening additives, and/or a polyol component. The polyol component comprises an ester polyol and petroleum polyol component. The hydroxyl value (HV) of the ester polyol determines the ester polyol replacement level of the resultant foam or coating. The ester polyol comprises about 10% to about 100% of the polyol component. The hydroxyl value (HV) of the ester polyol can be fine tuned by the selection of the difunctional monofunctional ratio (DMR) and hydroxyl:carboxyl ratio (HCR) of the starting ozone acids.

Example 4

Preparation of Ester Polyols from Full Composition PFAD Virtual Ozone Acids Using Glycerin, TMP and Me-PG A series of ester polyols were prepared from full composition PFAD virtual ozone acids with the primary polyols glycerin, TMP and Me-PG while varying the hydroxyl/carboxyl ratios from 1.85 to 1.10. Table I shows the polyol compositions and the values of physical parameters such as HV, AV, COT, viscosity, and percent volatilization used to determine the applicability of these polyols to prepare useful products.

TABLE I

Properties of full composition PFAD virtual ozone acids using glycerin, TMP and Me-PG

| Polyol No. (LRB 52729) | PFAD Virtual Ozone Acids | | | | | Wt. % Oz. Acids | Glycerin | | | |
|---|---|---|---|---|---|---|---|---|---|---|
| | Grams | Mole Diacid | Mole Mono- | Di: Mono | Total Mole $CO_2H$ | | Grams | Mole | Mole OH Grps. | Wt. % Glyc. |
| 2 (17-10) | 96.73 | 0.1498 | 0.3300 | 32.68 | 0.6296 | 67.92 | 14.49 | 0.1573 | 0.4720 | 10.17 |
| 11 (55-30) | 96.73 | 0.1498 | 0.3300 | 32.68 | 0.6296 | 65.9 | 0.00 | 0.00 | 0.00 | 0.00 |
| 11R (84-27) | Ditto | Ditto | Ditto | Ditto | Ditto | Ditto | Ditto | Ditto | Ditto | Ditto |
| 14 (73-27) | 96.73 | 0.1498 | 0.3300 | 32.68 | 0.6296 | 65.00 | 0.00 | 0.00 | 0.00 | 0.00 |
| 10 (51-23) | 96.79 | 0.1498 | 0.3307 | 32.68 | 0.6296 | 75.04 | 10.258 | 0.1114 | 0.3342 | 7.95 |
| 12 (63-20) | 96.79 | 0.1498 | 0.3307 | 32.68 | 0.6296 | 72.45 | 0.00 | 0.00 | 0.00 | 0.00 |
| 15 (77.25) | 96.79 | 0.1498 | 0.3307 | 32.68 | 0.6296 | 72.56 | 0.00 | 0.00 | 0.00 | 0.00 |
| 13 (67-15) | 96.79 | 0.1498 | 0.3307 | 32.68 | 0.6296 | 75.64 | 0.00 | 0.00 | 0.00 | 0.00 |

| Polyol No. (LRB 52729) | Me-PG and(or) TMP | | | | | Total Mole OH | Total Mole OH/Total Mole $CO_2H$ |
|---|---|---|---|---|---|---|---|
| | Species | Grams | Mole | Mole OH | Wt. % | | |
| 2 (17-10) | Me-PG | 31.20 | 0.3462 | 0.6924 | 21.90 | 1.1644 | 1.85 |
| | IBAnh | 10.45 | | | | | |
| 11 (55-30) | Me-PG | 31.20 | 0.3472 | 0.6924 | 20.90 | 1.1644 | 1.85 |
| | TMP | 21.11 | 0.1573 | 0.4720 | 14.20 | | |
| 11R (84-27) | Me-PG | Ditto | Ditto | Ditto | Ditto | Ditto | 1.85 |
| | TMP | | | | | | |
| 14 (73-27) | TMP | 52.08 | 0.3881 | 1.1644 | 35.00 | 1.1644 | 1.85 |
| 10 (51-23) | Me-PG | 21.93 | 0.2433 | 0.4866 | 17.00 | 0.8208 | 1.30 |
| 12 (63-20) | Me-PG | 21.93 | 0.2434 | 0.4687 | 16.43 | 0.8185 | 1.30 |
| | TMP | 14.84 | 0.1106 | 0.3318 | 11.12 | | |
| 15 (77.25) | TMP | 36.61 | 0.2783 | 0.8185 | 27.44 | 0.8185 | 1.30 |
| 13 (67-15) | Me-PG | 18.49 | 0.2063 | 0.4125 | 14.54 | 0.6933 | 1.10 |
| | TMP | 12.56 | 0.0936 | 0.2808 | 9.82 | | |

TABLE I-continued

Properties of full composition PFAD virtual ozone acids using glycerin, TMP and Me-PG

| Polyol No. (LRB 52729) | Physical State | | Cryst. Onzet T. (° C.) | Viscosity (cP) | TGA 1st Der. Peaks (° C.) | Wt. Loss at 250° C. for 90 Minutes |
|---|---|---|---|---|---|---|
| | Initial | 2/9/09 | HV/AV | | | |
| 2 (17-10) | Approxiable SOLID | Approxiable SOLID | | | | |
| 11 (55-30) | Clear Liq. | Clear Liq. | 204/0.0 | 6.26 | 67.9 | 1.30-10% 3.20-30% 4.40-60% | 53% |
| 11R (84-27) | Clear Liq. | Clear Liq. | 257/0.28 | 5.31 | 69.9 | | 6.1% |
| 14 (73-27) | Clear Liq. | Turbid 1/7 Thick 1/11 | 2.28/0.83 | 4.87 | 300.3 | | 28% |
| 10 (51-21) | Approxiable SOLID | Approxiable SOLID | 93.5/8.28 | | | | |
| 13 63-20) | Clear Liq. | Clear Liq. | 83.5/0.0 | 5.84 | 66.5 | | 33% |
| 15 77-25) | Clear Liq. | Clear Liq. | 84.8/0.83 | 4.96 | 33.5 | | |
| 15R 92-31f | Clear Liq. | Clear Liq. | 99.2/0.0 | 4.35 | 33.3 | | 10.5 |
| 13 (67-15) | Clear Liq. | Clear Liq. | 30.5/0.0 | 4.68 | 85.9 | | 26% |

| Polyol No. (LRB 52729) | GPC | Comments |
|---|---|---|
| 2 (17-10) | | |
| 11 (55-30) | 8.78/5.37/ 195 | Exact mole replacement of glycerin No. 2 with TMP while keeping Me-PG the same. <5B and 2B coadings with TD1 and HDL respectivaly. |
| 11R (84-27) | Sh./8.57/ 526/Sh. | Repeat reaction of 52729-55-90. 5B coading with TD1 and 1H coading with HDL |
| 14 (73-27) | Sh./9.34/ 573/254 | Same total OH provided by TMP as Me-PG & TMP in No. 12 |
| 10 (51-21) | | Same ratio at Glyserine/Me-PG at No. 2 |
| 13 63-20) | | Exact node replacement of glyserine at No. 10 with TMP while keeping Me-PG the same. <5B and 5B coadings with TDI and HDL respectivaly. |
| 15 77-25) | 1732/ Sh (low)) | Same total OH previously TMP as Me-PG & TMP is No. 12. <5B and 5B coading with TDL and HDL respectively. |
| 15R 92-31f | 1775.Sh. | Sent to Troy as flexible foarm candidate. |
| 13 (67-15) | 10.36/928 | GPC shows a member of shoulders at MW <928 explaining relatively high weight 1 cms at 250 C. Flexible foam candidate |

Polyols 2, 11 and 14.

As shown in Table I, polyols 2, 11 and 14 all incorporated a hydroxyl/carboxyl ratio of 1.85. It is instructive that polyol 2, which uses a mixture of glycerin and Me-PG as the primary polyols, produced a polyol that was mainly solid. However, polyol 11 and 11R (its repeat preparation at larger scale), which was nearly identical to polyol 10 except that it employed an exact mole replacement of glycerin with TMP, was a liquid that has yet to precipitate any solid. However, polyol 14 which is similar to polyol 11 except that the Me-PG component was replaced with an equal molar amount of TMP, was a turbid, thick material that eventually precipitated solid. Following are conclusions obtained from these polyol properties:

TMP is significantly better than glycerin in maintaining phase homogeneity in full palm composition polyols (as observed previously in polyols from fractionated PFAD compositions)

A mixture of TMP and Me-PG is better than TMP alone in maintaining polyol phase homogeneity Polyols 10, 12 & 15.

As shown in Table I, polyols 10, 12 and 15 all incorporated an hydroxyl/carboxyl ratio of 1.30. It can be seen that polyol 10 that employed glycerin and Me-PG as the primary polyols was essentially a solid. However, polyol 12 which was identical to polyol 10 except that it employed an exact mole replacement of glycerin with TMP was a liquid that has yet to develop solid. Polyol 15 and 15R (its repeat large scale preparation) was similar to polyol 12 except that the Me-PG was replaced with an exact molar amount of TMP and was initially a liquid that has maintained its phase homogeneity with time. The implication of these results is that at lower hydroxyl/carboxyl ratios, the dependence of phase homogeneity on total replacement of Me-PG with TMP is not as sensitive as in higher hydroxyl/carboxyl ratio. This could be due to the fact that at higher ratios, the polyol molecular weights are smaller so there is a higher probability that fully saturated will not be bound to a sufficient amount (or any) solubilizing substituents.

A polyurethane coating was prepared form polyol 11 using hexamethylene diisocyanate (HDI) which was found to have a 1H hardness and good gloss values. This is in contrast to only obtaining a 5B hardness when this polyol was cured with toluene diisocyanate (TDI).

Example 5: Rigid Foam Polyols Using Feedstock (Tallow)

To confirm the process scalability and product consistency, 18 L scale reactor runs have been performed to synthesize rigid foam polyols by using the tallow-based fatty acids as the feedstock. The amount of feedstock and other components were weighed (as shown in Table 100) and charged into an 18 L glass reactor. The mixture was stirred using an overhead stirrer and heated to 180° C. to ensure all components dissolved and homogenized. The temperature was then increased to between 210° C.-220° C. and water was removed throughout the reaction. The reaction was monitored by the reduction in acid value (AV). Towards the end of the reaction, the rate of AV reduction was observed to decrease. To facilitate the removal of traces of water and acids, an inert gas sparge was introduced into each reactions. The reactions were stopped and considered complete when the AV reached 3 mg KOH/g or below. The resultant polyols have the following properties as shown in Table 200.

TABLE 100

18 L Runs on Rigid Polyols using tallow based feedstock

| Reactant | Target mass, g | Actual mass, g | | |
|---|---|---|---|---|
| | | Run 1 | Run 2 | Run 3 |
| Azelaic acid (tallow-based) | 5411.71 | 5411.64 | 5413.94 | 5412.88 |
| Nonanoic acid (tallow-based) | 5844.01 | 5844.36 | 5845.00 | 5848.03 |
| Glycerin | 4892.42 | 4908.23 | 4894.64 | 4892.89 |
| Sorbitol | 2886.42 | 2895.81 | 2887.29 | 2888.44 |
| Tin (II) Oxalate (catalyst) | 33.61 | 34.06 | 34.08 | 36.00 |

TABLE 200

Resultant Polyol Properties from the 18 L bench scale runs

| Reaction | Run 1 | Run 2 | Run 3 |
|---|---|---|---|
| Acid Value (mgKOH/g) | 2.02 | 2.20 | 0.49 |
| Hydroxyl Value (mgKOH/g) | 443.40 | 401.40 | 420.30 |
| % mol Gly | 10.47 | 10.42 | 9.34 |
| % mol Mono-gly | 39.05 | 38.78 | 38.84 |
| % mol Di-gly | 41.40 | 42.39 | 42.74 |
| % mol Sorb | 9.09 | 8.41 | 9.08 |
| 1°/2° OH | 1.04 | 1.06 | 1.03 |

The foams produced from the polyol generated in 18 liter runs 1, 2, and 3 were satisfactory in producing rigid foams. Independent analysis performed at an external laboratory showed that the product foams are well suited for rigid foam formulations for thermal insulation properties. The comparison was done against a petroleum-based polyol using a similar foam formulation. The summary of the main properties of rigid foam performance are as shown in Table 300 below.

TABLE 300

PU foam performance using Rigid Run 1, Rigid Run 2 and Rigid Run 3

| Polyols | Density (kg/m³) | Apparent Dimensional Stability (after heating for 30 min.@ 120° C.) | Remarks |
|---|---|---|---|
| SG 360 | 32.20 | Hard @ 120° C., no deformation | Petroleum based/reference |
| Run 1 | 32.84 | Hard @ 120° C., no deformation | 18 L tallow-based |
| Run 2 | 32.68 | Hard @ 120° C., no deformation | 18 L tallow-based |
| Run 3 | 32.20 | Hard @ 120° C., no deformation | 18 L tallow-based |

Example 6: Runs Using Palm-Based Feedstock

Palm-based azelaic and nonanoic acids were weighed into a 500 ml four neck round bottom flask at specific amounts as shown in Table 400 for their respective applications. The mixture was stirred using an overhead stirrer and heated to 180° C. to ensure all components dissolved and homogenized. The temperature was then increased between 210° C.-220° C. and water was removed throughout the reaction. The reaction was monitored by acid value (AV) reduction. Towards the end of the reaction, the rate of AV reduction decreased. To facilitate traces of water and acids removal, an inert gas sparge was introduced into the reaction. The reaction was stopped and considered complete when the AV reached 3 mg KOH/g or below. The resultant polyols have the following properties as shown in Table 500.

TABLE 400

Compositions by weight for polyester polyols lab scale synthesis using actual palm-based feedstock

| Product | Rigid wt (g) | Flexible wt (g) | Case wt (g) |
|---|---|---|---|
| Azelaic Acid | 69.78 | 84.3 | 74.65 |
| Pelargonic Acid | 74.65 | 107.95 | 78.3 |
| Glycerin | 66.28 | 48.95 | — |
| Sorbitol | 39.33 | — | — |
| 2-methyl-1,3-propanediol | — | 88 | 27.58 |
| TMP | — | — | 69.48 |
| Tin (II) Oxide | 0.075 | 0.075 | 0.075 |

TABLE 500

Properties of Lab Scale Palm Based Polyester Polyols for all 3 applications - Rigid, Flexible and Coating

| Properties | Test method | Rigid Polyols | Flex Polyols | Coating Polyols |
|---|---|---|---|---|
| Acid Value, mg KOH/g | ASTM D 4662-08 | 0.7 | 0.9 | 0.52 |
| Hydroxyl Value, mg KOH/g | ASTM D 4274-05 | 405 | 53.3 | 208 |
| Moisture, % | ASTM D 4672-00 | 0.026 | 0.021 | 0.022 |
| Viscosity @ 25.0° C., cps | ASTM D 4878-08 | 2448 | 1116 | 650 |
| MW | GPC | 881 | 4749 | 1292 |
| Functionality | — | 6.4 | 4.5 | 4.8 |
| Color | Gardner | 6.3 | 5.8 | 3.9 |
| Solubility in Ethyl Acetate, 50/50 by wt | — | — | — | Soluble |

TABLE 500-continued

Properties of Lab Scale Palm Based Polyester Polyols for all 3 applications - Rigid, Flexible and Coating

| Properties | Test method | Rigid Polyols | Flex Polyols | Coating Polyols |
|---|---|---|---|---|
| Viscosity of 50/50 ethyl acetate solution | — | — | — | 5 cPs @23° C. |

The following tables 600 to 1000 show properties of products obtained from the process of Example 6.

Final Product Formulation and Analysis

1) Palm Based Rigid Foam Formulation and Properties

TABLE 600

Formulations and Foaming Profiles of Rigid PU Foams Based on Palm-based Rigid Polyols. Prepared with Water as a Sole Blowing Agent

| Designation | Eqv. Weight | 100% Petroleum | 50% re-placement | 100% re-placement |
|---|---|---|---|---|
| Polyol system | | | | |
| Poly-G 74-376 (Petroleum based) | 150.4 | 100 | 50 | 0 |
| Rigid, Palm-based | 135.2 | — | 50 | 100 |
| Water | 9 | 4.5 | 4.5 | 4.5 |
| Surfactant | 748 | 2.5 | 2.5 | 2.5 |
| Catalyst | 105 | 1.8 | 1.8 | 1.8 |
| Blowing agent catalyst | 233.7 | 0.1 | 0.1 | 0.1 |
| Polymeric MDI | 135.5 | 168.75 | 174.08 | 179.4 |
| Isocyanate Index | | 105 | 105 | 105 |
| Reaction Profile of Free-rise | | | | |
| Mix time, sec. | | 10 | 10 | 10 |
| Cream time, sec. | | 13 | 23 | 33 |
| Gel time, sec. | | 70 | 61 | 67 |
| Rise time, sec. | | 110 | 104 | 101 |
| Tack-free time, sec. | | 132 | 88 | 80 |
| Properties | | | | |
| Free-rise density, kg/m3 | | 32.36 | 34.44 | 35.08 |
| Apparent Dimensional Stability after heating for 30 min.@ 120° C. | | Hard @ 120° C. No deformation | Hard @ 120° C. No deformation | Hard @ 120° C. No deformation |

2) Palm-Based Flexible Foam Formulations and Properties

TABLE 700

Formulations and Foaming Profiles of Free-Rise Flexible Foams of Flex Palm Based Polyols

| Formulation | Eq Weight | 100% Petroleum Based | 10% Replacement | 20% Replacement | 30% Replacement | 50% Replacement | 75% Replacement |
|---|---|---|---|---|---|---|---|
| Poly-G 85-29 (Petroleum Based Polyols) | 2054.95 | 97 | 87.3 | 77.6 | 67.9 | 48.5 | 24.25 |
| Flex Palm Based Polyols | 1157.18 | 0 | 9.7 | 19.4 | 29.1 | 48.5 | 72.75 |
| Water | 9 | 3.6 | 3.6 | 3.6 | 3.6 | 3.6 | 3.6 |
| Cell Opener | 416.2 | 3 | 3 | 3 | 3 | 3 | 3 |
| Surfactant | 1335.7 | 1 | 1 | 1 | 1 | 1 | 1 |
| Catalyst | 105 | 0.8 | 0.8 | 0.8 | 0.8 | 0.8 | 1 |
| Chain Extender | 35.04 | 1 | 1 | 1 | 1 | 1 | 1 |
| Blowing agent catalyst | 233.7 | 0.1 | 0.1 | 0.1 | 0.1 | 0.1 | 0.1 |
| Isocyanate System | | | | | | | |
| 2,4'-rich diphenylmethane diisocyanate | 128.83 | 57.02 | 57.44 | 57.87 | 58.29 | 59.14 | 60.42 |
| Isocyanate Index | | 90 | 90 | 90 | 90 | 90 | 90 |
| Reaction Profile | | | | | | | |
| Mix time, sec. | | 7 | 7 | 7 | 7 | 7 | 7 |
| Cream time, sec. | | 12 | 12 | 11 | 12 | 16 | 17 |
| Gel time, sec. | | 44 | 45 | 52 | 56 | 60 | — |
| Rise time, sec. | | 74 | 74 | 86 | 86 | 87 | — |
| Post-curing time & temp. | | 30 min @ 80° C. | 30 min @ 80° C. | 30 min @ 80° C. | 30 min @ 80° C. | 30 min @ 80° C. | 0 min @ 80° C. |
| Properties | | | | | | | |
| Free-rise density, pcf | | 2.47 | 2.56 | 2.45 | 2.42 | 2.47 | — |
| Cell Structure | | Uniform | Uniform | Uniform | Uniform | Uniform | Collapse |

TABLE 800

Properties of Free Rise Foams Based on Flex Palm Based Polyol

| | 0 (100% Petroleum Based) | 10 | 20 | 30 | 50 |
|---|---|---|---|---|---|
| Flex Palm Based Polyol, % | | | | | |
| Density, kg/m3 | 2.47 | 2.56 | 2.45 | 2.42 | 2.47 |
| Resilience, Ball (16 mm) Rebound, % | 57.2 ± 0.9 | 53.6 ± 0.6 | 47.8 ± 0.7 | 42.9 ± 1.7 | 37.3 ± 1.4 |
| Tensile Strength, psi | 11.67 ± 0.48 | 11.03 ± 1.65 | 10.75 ± 0.79 | 11.08 ± 1.04 | 10.03 ± 0.95 |
| Elongation at Break, % | 136 ± 7 | 118 ± 11 | 134 ± 9 | 130 ± 14 | 115 ± 9 |
| Hysteresis, % | 35.3 ± 0.9 | 36.0 ± 0.4 | 41.3 ± 0.9 | 43.0 ± 0.9 | 47.7 ± 0.5 |
| Compression Force Deflection, kPa | | | | | |
| @ 25%, Deflection | 2.21 ± 0.14 | 2.14 ± 0.07 | 2.48 ± 0.28 | 2.28 ± 0.28 | 2.48 ± 0.34 |
| @ 50%, Deflection | 3.79 ± 0.21 | 3.72 ± 0.07 | 4.14 ± 0.48 | 3.79 ± 0.34 | 4.27 ± 0.76 |
| @ 65%, Deflection | 6.83 ± 0.41 | 6.62 ± 0.07 | 7.24 ± 1.10 | 6.76 ± 0.55 | 7.72 ± 1.38 |
| Compression Strength Ratio | | | | | |
| Deflection/25% 50% Deflection | | | | | |
| Deflection/25% 65% Deflection | 1.71 3.09 | 1.74 3.09 | 1.67 2.92 | 1.66 2.96 | 1.72 3.11 |
| Cell Structure | Uniform | Uniform | Uniform | Uniform | Uniform |

TABLE 900

Properties of coatings based on Palm Based Coating Polyols at different Isocyanate Index

| Coating Designation | Formulation 1 | Formulation 2 |
|---|---|---|
| Polyol system, g* | | |
| Palm Based Coating Polyol | 12.48 | 12.48 |
| Catalyst | 0.006 | 0.006 |
| Solvent | 25.0 | 21.67 |
| Isocyanate | 12.1 | 13.31 |
| Isocyanate Index | 1.00 | 1.10 |
| Mix time @ 2200 RPM, sec. | 20 | 20 |
| Coating solution | | |
| Appearance | Transparent | Transparent |
| Solid content, % | 43 | 50 |
| Film properties | | |
| Tensile Strength, psi | 485 ± 11 | 765 ± 47 |
| Elongation at Break, % | 98 ± 11 | 103 ± 4 |
| Impact Testing, ASTM D2794 | — | No cracks; |
| Pencil Hardness, ASTM 3363 | — | HB |
| Adhesion Test, ASTM 3359, Method B | — | (5A) No peeling or removal |
| Adhesion Test, ASTM 3359, Method B after Humidity exposure per ASTM D2247 | — | 5A) No peeling or removal |
| Solvent Resistance Test | | |
| MEK, weight gain/loss, % | — | 51.3 |
| Toluene, weight gain/loss, % | — | 47.9 |
| 0.1N NaOH, pH 13, weight gain/loss, % | — | 1.5 |
| 0.1N HCl, pH 1, weight gain/loss, % | — | −0.2 |
| Weight gain/loss, % after Humidity exposure per ASTM D2247 | — | Negligible |
| Comments | Nice coating; Good curing; | Nice coating; Good curing. |

TABLE 1000

Properties of coatings solution based on Palm Based Coating Polyol at different Isocyanate Index

| | Formulation 1 | Formulation 2 |
|---|---|---|
| Polyol system, g | | |
| Palm Based Coating Polyol | 12.48 | 12.48 |
| Catalyst | 0.006 | 0.006 |
| Solvent | 25.0 | 21.67 |
| Isocyanate | 12.1 | 13.31 |
| Isocyanate Index | 1.00 | 1.10 |
| Mix time @ 2200 RPM, sec. | 20 | 20 |
| Coating solution | | |
| Solid content, % | 43 | 50 |
| Appearance | Transparent | Transparent |
| Viscosity after 10 min., cps | 10 cps @ 31.2° C. | 15 cps @ 29° C. |
| Viscosity after 30 min., cps | 53 cps @ 26° C. | 170 cps @ 28° C. |
| Film properties after 24 hours | Nice coating; Good curing | Nice coating Good curing |

The subject matter claimed herein is not limited to embodiments that solve any disadvantages or that operate only in environments such as those described above. Rather, this background is only provided to illustrate on exemplary technology area where some embodiments described herein may be practiced. Bibliographic references mentioned in the present specification are for convenience listed in the form of a list of references and added at the end of the examples. The whole content of such bibliographic references is herein incorporated by reference.

REFERENCES

1. WO2007027223
2. U.S. Pre-Grant Publication No. 2005/0112267
3. U.S. Pat. No. 7,125,950
4. US Patent Application No. US 2006/0194974
5. U.S. Pat. No. 2,813,113

The invention claimed is:

1. A method of preparing a plurality of ester polyols, comprising:
    subjecting palm fatty acid distillate to oxidative ozonolysis to form a mixture comprising azelaic acid and a plurality of monocarboxylic acids;
    esterifying the mixture formed during said subjecting step with at least two branched primary polyols to produce a plurality of ester polyols,
    wherein the at least two branched primary polyols comprise 2-methyl-1,3-propanediol (2-MePG) and trimethylolpropane (TMP);
    wherein the mixture and the at least two branched primary polyols comprise a reaction mixture having a hydroxyl/carboxyl ratio corresponding to a ratio of moles of OH groups to moles of —COOH groups, wherein the hydroxyl/carboxyl ratio is from about 1.10 to about 1.85; and
    wherein the plurality of ester polyols are produced in the form of a composition that contains the plurality of ester polyols present in a single phase.

2. The method of preparing a plurality of ester polyols according to claim 1, wherein the method further comprises esterifying the mixture comprising azelaic acid and the plurality of monocarboxylic acids with at least one unbranched primary alcohol.

3. A method of preparing a plurality of ester polyol esters, the method comprising:
    preparing the plurality of ester polyols according to the method of claim 1, and
    further esterifying the plurality of ester polyols with at least one carboxylic acid to produce a plurality of ester polyol esters.

4. The method according to claim 1, wherein the method further comprises esterifying the mixture comprising azelaic acid and the plurality of monocarboxylic acids with at least two unbranched primary polyols.

5. The method according to claim 4, wherein at least one of the at least two unbranched primary polyols is selected from the group consisting of glycerol, sorbitol, xylitol, erythritol, and a mixture of two or more thereof.

6. The method according to claim 1, wherein the plurality of ester polyols have a hydroxyl value (HV) ranging from about 30.5 mg KOH/g to about 257 mg KOH/g.

7. A composition comprising a plurality of ester polyols in a single phase, wherein the plurality of ester polyols comprise the reaction product of:
    a mixture comprising azelaic acid, a plurality of monocarboxylic acids, and at least two branched primary polyols that comprise 2-methyl-1,3-propanediol (2-MePG) and trimethylolpropane (TMP),
    wherein the azelaic acid and the plurality of monocarboxylic acids that form part of said mixture are obtained as a product of oxidative ozonolysis of palm fatty acid distillate, which product of oxidative ozonolysis is mixed with the at least two branched primary polyols to form said mixture; and
    wherein the mixture has a hydroxyl/carboxyl ratio corresponding to a ratio of moles of —OH groups to moles of —COOH groups, wherein the hydroxyl/carboxyl ratio is from about 1.10 to about 1.85.

8. The composition according to claim 7, wherein the plurality of ester polyols further comprises the reaction product of at least one unbranched primary polyol with the mixture comprising azelaic acid and the plurality of monocarboxylic acids.

9. The composition according to claim 8, wherein the at least one unbranched primary polyol is selected from the group consisting of glycerol, sorbitol, xylitol, erythritol, and a mixture of two or more thereof.

10. The composition according to claim 7, wherein the plurality of ester polyols have a hydroxyl value (HV) from about 30.5 mg KOH/g to about 257 mg KOH/g.

11. A foam, wherein the foam is prepared from a composition that comprises a plurality of ester polyols present in a single phase, wherein the composition comprising the plurality of ester polyols is the reaction product of:
    a mixture comprising azelaic acid, a plurality of monocarboxylic acids and at least two branched primary polyols that comprise 2-methyl-1,3-propanediol (2-MePG) and trimethylolpropane (TMP);
    wherein the azelaic acid and the plurality of monocarboxylic acids that form part of said mixture are obtained as a product of oxidative ozonolysis of palm fatty acid distillate, which product of oxidative ozonolysis is mixed with the at least two branched primary polyols to form said mixture;
    wherein the mixture has a hydroxyl/carboxyl ratio corresponding to a ratio of moles of —OH groups to moles of —COOH groups, wherein the hydroxyl/carboxyl ratio is from about 1.10 to about 1.85.

12. The foam according to claim 11, wherein the mixture further comprises at least one unbranched polyol and the plurality of ester polyols used to prepare the foam further comprises the product of azelaic acid and the plurality of monocarboxylic acids reacted with the at least one unbranched primary polyol.

13. The foam according to claim 11, wherein the foam is prepared with a polyol reaction mixture comprising about 10 wt % to about 100 wt % of the plurality of ester polyols and, optionally, about 90 wt % to about 0 wt % of a petroleum polyol.

14. The foam according to claim 11, wherein the plurality of ester polyols have a hydroxyl value (HV) from about 30.5 mg KOH/g to about 257 mg KOH/g.

15. The foam according to claim 11, wherein the foam is a rigid foam or a flexible foam.

16. The foam according to claim 11, wherein the foam is prepared with at least one isocyanate.

17. A polyurethane coating prepared using the composition according to claim 7.

18. A method of reducing the separation of a composition comprising a plurality of ester polyols in a single phase into two or more phases, the method comprising:
    subjecting palm fatty acid distillate to oxidative ozonolysis to form a mixture of azelaic acid and a plurality of monocarboxylic acids;
    esterifying the mixture formed during said subjecting step with at least two branched primary polyols to produce a composition comprising a plurality of ester polyols, wherein the at least two branched primary polyols comprise 2-methyl-1,3-propanediol (2-MePG) and trimethylolpropane (TMP);
    wherein the mixture and the at least two branched primary polyols comprise a reaction mixture having a hydroxyl/carboxyl ratio corresponding to a ratio of moles of —OH groups to moles of —COOH groups, wherein the hydroxyl/carboxyl ratio is from about 1.10 to about 1.85, whereby said esterifying reduces the phase separation of the plurality of ester polyols.

19. The method of claim 18, wherein the method further comprises esterifying the mixture comprising azelaic acid and the plurality of monocarboxylic acids with at least one unbranched primary polyol.

20. The method according to claim 18, wherein the composition has a temperature in the range from about 20° C. to about 80° C.

21. The method according to claim 1, wherein the palm fatty acid distillate is a fractionated palm fatty acid distillate or a full composition palm oil fatty acid distillate.

22. The composition according to claim 7, wherein the palm fatty acid distillate is a fractionated palm fatty acid distillate or a full composition palm oil fatty acid distillate.

23. The foam according to claim 11, wherein the palm fatty acid distillate is a fractionated palm fatty acid distillate or a full composition palm oil fatty acid distillate.

24. The method according to claim 18, wherein the palm fatty acid distillate is a fractionated palm fatty acid distillate or a full composition palm oil fatty acid distillate.

* * * * *

UNITED STATES PATENT AND TRADEMARK OFFICE
CERTIFICATE OF CORRECTION

| | | |
|---|---|---|
| PATENT NO. | : 10,654,791 B2 | Page 1 of 1 |
| APPLICATION NO. | : 14/381554 | |
| DATED | : May 19, 2020 | |
| INVENTOR(S) | : Garbark et al. | |

It is certified that error appears in the above-identified patent and that said Letters Patent is hereby corrected as shown below:

In Claim 1, at Column 35, Line 15, delete "OH" and insert -- –OH --.

Signed and Sealed this
Twenty-ninth Day of September, 2020

Andrei Iancu
*Director of the United States Patent and Trademark Office*